US008829044B2

(12) United States Patent
Park et al.

(10) Patent No.: US 8,829,044 B2
(45) Date of Patent: *Sep. 9, 2014

(54) STABILIZED VITAMIN C DERIVATIVES HAVING A PEPTIDE MOLECULE, PREPARATION METHOD THEREOF, AND COMPOSITION CONTAINING THE SAME

(75) Inventors: Jong-Il Park, Daejeon (KR); Heung-Jae Kim, Daejeon (KR); Dong-Won Kim, Daejeon (KR); Chae-Jin Lim, Daejeon (KR); Jong-Phil Kang, Daejeon (KR); Kyeong-Yong Park, Daejeon (KR); Seok-Jeong Yoon, Daejeon (KR); Seon-Deok Kwon, Daejeon (KR); Ho-Il Choi, Daejeon (KR)

(73) Assignee: Peotron Co. Ltd. (KR)

( * ) Notice: Subject to any disclaimer, the term of this patent is extended or adjusted under 35 U.S.C. 154(b) by 1610 days.

This patent is subject to a terminal disclaimer.

(21) Appl. No.: 12/308,604

(22) PCT Filed: Sep. 5, 2006

(86) PCT No.: PCT/KR2006/003520
§ 371 (c)(1),
(2), (4) Date: Sep. 15, 2010

(87) PCT Pub. No.: WO2007/148847
PCT Pub. Date: Dec. 27, 2007

(65) Prior Publication Data
US 2010/0331260 A1  Dec. 30, 2010

(30) Foreign Application Priority Data
Jun. 22, 2006  (KR) .................. 10-2006-0056580

(51) Int. Cl.
*A61K 31/375* (2006.01)
*C07K 5/08* (2006.01)
*C07K 5/10* (2006.01)
*G01N 33/82* (2006.01)

(52) U.S. Cl.
USPC ........... 514/474; 436/93; 514/21.9; 530/331; 530/330

(58) Field of Classification Search
None
See application file for complete search history.

(56) References Cited

U.S. PATENT DOCUMENTS

| 5,767,149 A | 6/1998 | Yamamoto et al. |
| 7,521,477 B2 * | 4/2009 | Choi et al. .................... 514/474 |
| 2003/0143172 A1 * | 7/2003 | Ito et al. ....................... 424/70.1 |
| 2007/0140998 A1 | 6/2007 | Kato et al. |

FOREIGN PATENT DOCUMENTS

| EP | 0875514 A1 | 11/1998 |
| FR | 2855047 A1 | 11/2004 |
| JP | 03-139288 A | 6/1991 |
| JP | WO-2005/034903 | * 4/2005 |
| JP | 2005-336156 A | 12/2005 |
| KR | WO-2004/096837 | * 11/2004 |
| WO | WO-2004/096837 A1 | 11/2004 |
| WO | WO 2004096837 | * 11/2004 |
| WO | WO-2005/034903 A1 | 4/2005 |

OTHER PUBLICATIONS

Website: http://www.skinacea.com/skincare/anti-aging.html, 9 pages, retrieved on May 2, 2013.*
"International Application Serial No. PCT/KR2006/003520, International Search Report mailed Apr. 18, 2007", 4 pgs.
"International Application Serial No. PCT/KR2006/003520, Written Opinion mailed Apr. 18, 2007", 3 pgs.
"European Application Serial No. 06783775.7, Supplementary European Search Report mailed Jan. 17, 2013", 8 pgs.

* cited by examiner

*Primary Examiner* — Satyanarayana R Gudibande
(74) *Attorney, Agent, or Firm* — Schwegman, Lundberg & Woessner, P.A.

(57) ABSTRACT

The present invention relates to a stabilized vitamin C derivative with a peptide molecule linked to vitamin C or a pharmaceutically acceptable salt thereof, a method of preparing the same, and a composition containing the same.

24 Claims, 2 Drawing Sheets

STABILIZED VITAMIN C DERIVATIVES HAVING A PEPTIDE MOLECULE, PREPARATION METHOD THEREOF, AND COMPOSITION CONTAINING THE SAME

CROSS REFERENCE TO RELATED APPLICATION

This application is a nationalization under 35 U.S.C. 371 of PCT/KR2006/003520, filed Sep. 5, 2006 and published as WO 2007/148847 A1 on Dec. 27, 2007, which application claims priority to and the benefit of Korean Patent Application No. 10-2006-0056580 filed on Jun. 22, 2006, which applications and publication are incorporated herein by reference and made a part hereof.

BACKGROUND OF THE INVENTION (a) Field of the Invention

The present invention relates to a stabilized vitamin C derivative having a peptide molecule or a pharmaceutically acceptable salt thereof, a preparation method of the vitamin C derivative, and a composition containing the same.

(b) Description of the Related Art

Skin plays the roles of protection, barrier, body temperature regulation, excretion, respiration, and so forth, and consists of epidermis, dermis, and hypodermis. The epidermis is the thinnest layer, consisting of keratinocytes and melanocytes. The dermis accounts for about 95% of skin and is the layer that takes up skin moisturization and protection. It consists of collagen and elastin, which are protein fibers that play important roles in skin elasticity (or wrinkles). The dermis contains blood vessels, nerves, mast cells associated with allergic reactions, and natural moisturizing factors such as Na-PCA, hyaluronic acid, etc. The hypodermis supplies nutrients to the epidermis and the dermis, determines body shape, maintains body temperature, absorbs external impact, and protects the cells therebelow.

As skin ages, its functions decline rapidly because of endogenous or exogenous factors. As aging proceeds, the layers of the epidermis, the dermis, and the hypodermis become thin, and the collagen and elastin fibers become thinner and less elastic, resulting in wrinkles. Further, as the lipid composition and content in the lipid barrier that protects the skin changes, the moisture content in skin decreases, resulting in dryness and other physiological changes. Furthermore, melasma, freckles, pigmentation, and various other skin lesions are induced. In order to solve the skin aging-related problems, much research has been carried out on various active substances effective in skin improvement, and compositions containing them.

Antioxidant vitamins, such as vitamin C, vitamin E, β-carotene, and so on, have been used to inhibit skin aging. Among them, vitamin C is known to be effective in improving skin wrinkles, improving pigmentation problems such as melasma, freckles, dark spots, etc., and enhancing the immune system through protection from UV, antioxidant activity, and promotion of collagen formation. The functions of vitamin C in the body are as follows.

Vitamin C effectively blocks UV, particularly UV A [Darr, D. et al., 1996, *Acta Derm. Venereol.* (Strckh). 76: 264-268; Black, H. S. et al., 1975, *J. Invest. Dermatol.* 65: 412-414]. Also, vitamin C protects the skin from damage induced by UV B. When vitamin C is applied on the skins of pigs and humans and then UV B is irradiated thereon, it prevented erythema and sunburn (Darr, D. et al., 1992, *Brit. J. Dermatil.* 127: 247-253; Murry, J. et al., 1991, *J. Invest. Dermatol.* 96: 587).

Vitamin C acts as a strong antioxidant, which neutralizes the reactive oxygen species (ROS) generated in skin, blood, and other tissues by chemical contaminations, smoking, and particularly, UV. This is because of the structural characteristics of the vitamin C, which can accept two electrons and be readily oxidized to dehydro-L-ascorbic acid. Vitamin C is an important factor in the non-enzymatic antioxidant defense system of skin. When present in high concentration, vitamin C neutralizes such ROS as singlet oxygens, superoxide anions, hydroxy radicals, etc., before they oxidize or modify proteins, nucleic acids, cytoplasmic membrane lipids or other body constituents (Buettner, G. R. et al. 1996. Cadenas, E., Packer, L., eds. Handbook of antioxidants. pp. 91-115).

When administered percutaneously to the stratum corneum, vitamin C improves skin gloss and skin color, reduces wrinkles, and improves skin elasticity (U.S. Pat. No. 4,983, 382), because it promotes collagen synthesis. Hydroxyproline, which accounts for about 10% of collagen polypeptides, is synthesized by proline hydroxylase, wherein vitamin C acts as a cofactor of this enzyme (Tomita, Y. et al., 1980, *J. Invest. Dermatol.* 75(5): 379-382). That is, vitamin C activates proline hydroxylase to promote the synthesis of hydroxyproline, which in turn promotes the biosynthesis of the triple-helical collagen, thereby reducing skin wrinkles and improving skin condition.

Vitamin C offers a superior skin whitening effect, because it inhibits the activity of tyrosinase, which is important in producing melanin, and the production of melanin (Tomita, Y. et al., 1980, *J. Invset. Dermatol.* 75(5); 379-382).

In addition, vitamin C enhances the immune system by inhibiting the release of allergy-inducing histamine from the cell membrane, thereby preventing allergic reactions. It has been proven that vitamin C protects mice exposed to antigens from UV-induced immune suppression and resistance (Nakamura, T. et al., 1997, *J. Invest. Dermatol.* 109: 20-24).

Further, vitamin C helps the phagocytosis of leukocytes, facilitates the movements of leukocytes during infection to inhibit infection, promotes the biosynthesis of interferon, which is a protein that suppresses the proliferation of viruses, and improves resistance to a variety of infectious diseases. Further, vitamin C also participates in folic acid metabolism and amino acid metabolism.

Vitamin C is a water-soluble substance with the chemical formula $C_6H_8O_6$. Vitamin C is hydrophilic because of the hydroxyl groups present in C-2, C-3, C-5, and C-6 positions. In neutral pH, e.g., in water, the hydroxyl groups, particularly those in C-2 and C-3 positions, in Vitamin C becomes negatively charged, to be quickly and completely dissolved in aqueous solutions. However, under non-aqueous organic environments, e.g., in skin, vitamin C is not completely dissolved. Further, because vitamin C is not readily dissolved in the organic solvents commonly used in the external preparations, e.g., glycerin, propylene glycol, a variety of fats, etc., transdermal delivery of vitamin C is restricted. That is, in a non-ionized state, the pH should be maintained at 4.2 or lower in order for vitamin C to easily penetrate the skin barrier.

It is known that vitamin C is accumulated in skin 20 to 40 times higher when transdermally (externally) administered than orally administered. External preparations for improving wrinkles by UV blocking, antioxidation and promotion of collagen production, improving pigmentation problems such as melasma, freckles, dark spots, etc., and enhancing the immune system, should have a high degree of transdermal absorption because the active ingredients of the preparations need to reach the cells in the epidermis by passing through the stratum corneum of skin. In general, the degree of transdermal absorption of a substance relates to its lipophilicity. It is known that a substance having lipophilicity similar to that of skin is readily absorbed transdermally, because the partition coefficient into skin is high. In contrast, vitamin C is not readily absorbed transdermally because of high hydrophilicity and a low partition coefficient into skin.

There has been much research to improve safety, stability, and transdermal absorptivity of vitamin C.

Several types of vitamin C derivatives have been suggested. The first type of derivative is a phosphated ascorbic acid or a metal salt of phosphated ascorbic acid. This derivative is obtained by linking the hydroxyl group of the C-2 or C-3 position of ascorbic acid through an ester bond with the phosphate to form ascorbyl-2-phosphate or ascorbyl-3-phosphate, respectively. Compared with other derivatives, these derivatives are easily transited to L-ascorbic acid that can be utilized by the human body. However, they are not readily absorbed transdermally because they have negative charges.

The second type of derivative is an ascorbic acid bonded to a fatty acid. U.S. Pat. No. 5,409,693 discloses a vitamin C derivative in the form of a fat-soluble fatty acid ester of ascorbic acid, such as ascorbyl palmitate, ascorbyl laurate, ascorbyl myristate, ascorbyl stearate, etc. Among them, ascorbyl-6-palmitate is most frequently utilized. Although ascorbyl-6-palmitate is readily absorbed transdermally, it is not readily transited to L-ascorbic acid. It is reported that ascorbyl-6-palmitate failed in protecting the skin of mice from photo-oxidation (Bissett, D. et al., 1990, *Photodermatol Photoimmunol Photomed* 7: 56-62). There is another report that the treatment of skin with a serum containing 10 wt % ascorbyl-6-palmitate did not result in a significant increase of ascorbic acid (Pinnell, S. R. et al., 2001. *Dermatologic Surgery.* 27(2): 137-142).

The third type of derivative is ascorbic acid derivatives having a monosaccharide, such as glycosylated, mannosylated, fructosylated, fucosylated, galactosylated, N-acetylglucosaminated, or N-acetylmuraminated form. However, the physiological activities of these derivatives in the body have not yet been elucidated specifically and accurately.

The fourth type of derivative is an ascorbic acid bonded with a collagen-producing peptide. Korean Patent No. 0459679 discloses a derivative obtained by linking the hydroxyl group of the C-5 or C-6 position of ascorbic acid with a succinoyl group through an ester bond, and linking it with a collagen-producing peptide through an imide bond. This ascorbic acid derivative shows better efficiency than ascorbic acid, but is less stable.

Collagen is frequently found in skin, blood vessels, internal organs, bones, etc. It accounts for 70% of the dermis in skin. The fascia which surrounds muscles is made up of collagen. Collagen, which accounts about 30 wt % of the total proteins in the body, offers mechanical solidity to skin, confers resistance and binding strength of connective tissues, supports cell adhesion, and induces cell division and differentiation during growth or healing of wounds. Collagen is produced in fibroblasts. The amount of collagen decreases with natural aging and photo-aging. It is known that the amount of collagen decreases by 65% from the age of 20 to 80 (Shuster S., 1975, *British Journal of Dermatology*, 93(6): 639-643).

With the finding that activated collagen synthesis in the body increases the dermal matrix, resulting in the effects of improving wound healing, skin elasticity, wrinkle reduction, etc., collagen has been utilized in cosmetics, foods, medicines, and so forth. Some oligopeptides having less than 10 amino acids, which exist in collagen, are the smallest activation unit. They relate to functions as messenger, stimulator, and neurotransmitter, and take part in such physiological metabolisms as growth control, nursing, immunity, digestion, blood pressure, and healing. Particularly, peptides that are effective in skin regeneration are disclosed in French Patent No. 2,668,265, U.S. Pat. No. 4,665,054, WO91/3488, WO91/7431, and so forth. However, these peptides tend to form precipitates, thereby greatly reducing product stability.

Thus, the development of vitamin C derivatives with improved safety and stability and superior skin permeability is needed.

SUMMARY OF THE INVENTION

To satisfy the needs, the present invention intends to provide a vitamin C derivative with improved safety and stability and superior skin permeability by introducing a phosphate derivative and a peptide molecule, particularly a collagen-producing peptide, to vitamin C.

DETAILED DESCRIPTION OF THE PREFERRED EMBODIMENTS

Figure 1:
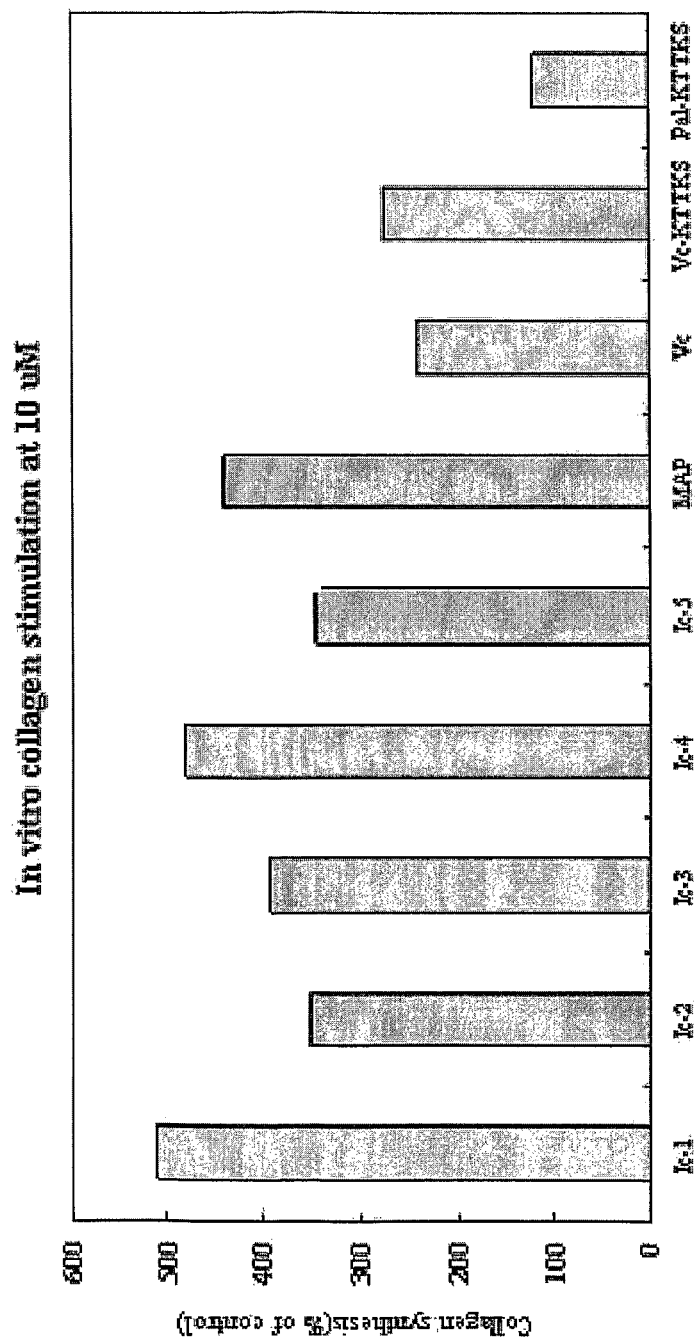
FIG. 1 shows a comparison of collagen biosynthesis capabilities using the compound of the present invention, vitamin C, magnesium ascorbyl phosphate, succinoyl ascorbyl pentapeptide, and palmitoyl pentapeptide.

A more complete appreciation of the invention, and many of the attendant advantages thereof, will be readily apparent as the same becomes better understood by reference to the following detailed description.

The present invention relates to a stabilized vitamin C derivative having a peptide molecule or a pharmaceutically acceptable salt thereof, a preparation method of the vitamin C derivative, and a composition containing the same.

The present invention relates to a stabilized vitamin C derivative in which a phosphoryl group or its derivative is introduced at the C-2 position, and a peptide, preferably a collagen-producing peptide, is introduced at the C-5 or C-6 position of vitamin C, or a pharmaceutically acceptable salt thereof.

In one aspect, the present invention relates to a stabilized vitamin C derivative with a peptide molecule, which is represented by the following Chemical Formula 1, and a pharmaceutically acceptable salt thereof:

(Chemical Formula 1)

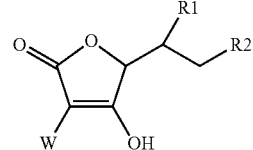

wherein

R1 and R2 are —OH or

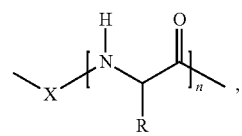

and are different from each other;

X is —OC(O)(CH$_2$)mC(O)—;

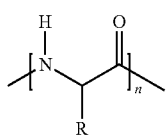

is a natural or non-natural peptide molecule, in which identical or different amino acid residues are linked through amide bonds, and the amino acid residues are selected from the group consisting of glycine, lysine, histidine, serine, proline, hydroxyproline, threonine, glutamic acid, methionine, glutamine, and arginine;

R is a side chain of the amino acid;

n is an integer between 3 and 10;

m is an integer between 2 and 5;

W is

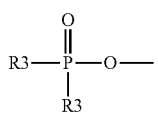

or glucose; and

R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

In a specific embodiment of the present invention, the compound represented by Chemical Formula 1 may be a compound represented by the following Chemical Formula 1a, 1b, 1c, or 1d:

[Chemical Formula 1a]

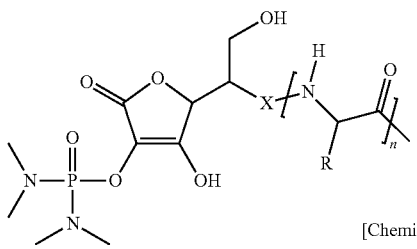

[Chemical Formula 1b]

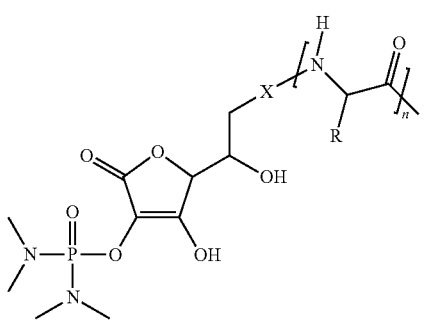

[Chemical Formula 1c]

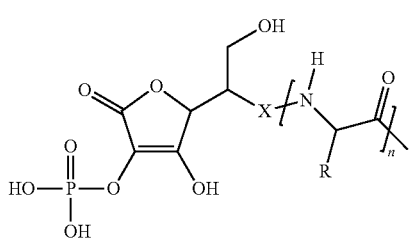

[Chemical Formula 1d]

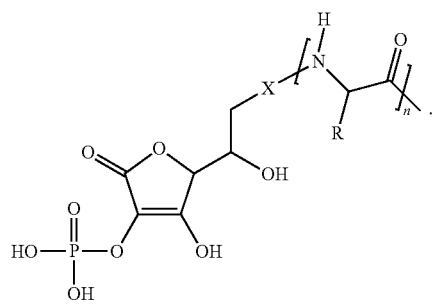

In a preferred embodiment of the present invention,

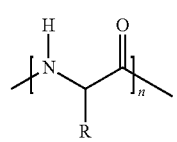

in Chemical Formula 1, 1a, 1b, 1c, or 1d is a peptide, in which identical or different amino acid residues selected from the group consisting of glycine, lysine, histidine, serine, proline, hydroxyproline, threonine, arginine, glutamine, methionine, and glutamic acid are linked through amide bonding;

R is a side chain of the amino acid residue; and n is an integer between 3 and 7.

In a more preferred embodiment, the peptide

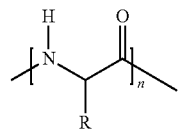

may be a tri-, tetra-, penta, or hepta-peptide, with n being an integer between 3 and 6, particularly a peptide selected from the group consisting of glycine-lysine-histidine, glycine-histidine-lysine, glycine-proline-hydroxyproline, lysine-threonine-threonine-lysine-serine, and glutamic acid-glutamic acid-methionine-glutamine-arginine-arginine.

X may be —OC(O)(CH$_2$)$_m$C(O)—, and m may be an integer between 2 and 4, more preferably 2 or 3.

Particularly preferably, X may be a succinyl group with m being 2.

In another aspect, the present invention relates to a stabilized vitamin C derivative having a peptide molecule represented by the following Chemical Formula 2, or a pharmaceutically acceptable salt thereof:

(Chemical Formula 2)

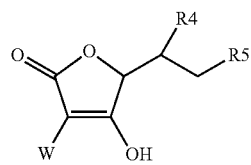

wherein

R4 and R5 are —OC(O)(CH$_2$)pCH$_3$, or

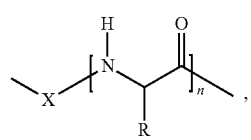

and are different from each other;

X is —OC(O)(CH$_2$)mC(O)—;

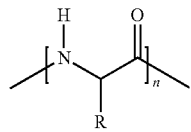

is a natural or non-natural peptide molecule in which identical or different amino acid residues are linked through amide bonds, and the amino acid residues are selected from the group consisting of glycine, lysine, histidine, serine, proline, hydroxyproline, threonine, glutamic acid, methionine, glutamine, and arginine;

R is a side chain of the amino acid;
n is an integer between 3 and 10;
m is an integer between 2 and 5;
p is an integer between 10 and 20;
W is

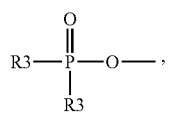

or glucose; and

R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

In a specific embodiment of the present invention, the compound represented by Chemical Formula 2 may be a compound represented by the following Chemical Formula 2a, 2b, 2c, or 2d:

[Chemical Formula 2a]

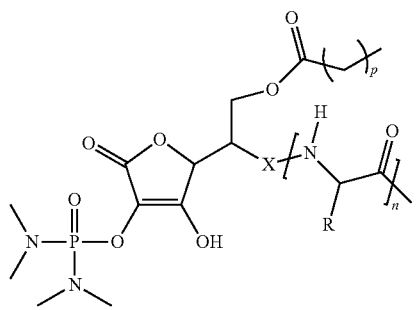

[Chemical Formula 2b]

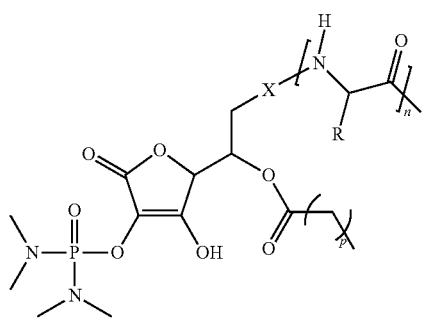

[Chemical Formula 2c]

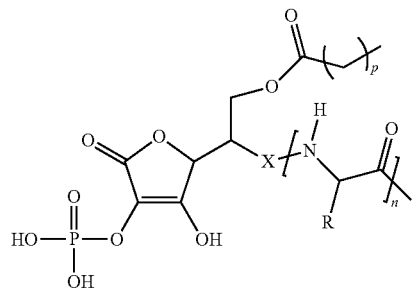

[Chemical Formula 2d]

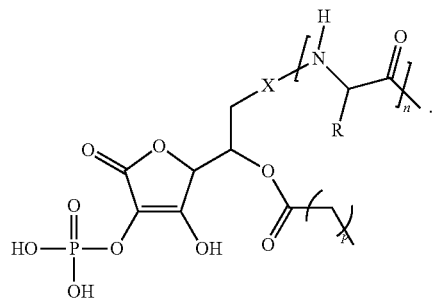

In a preferred embodiment of the present invention,

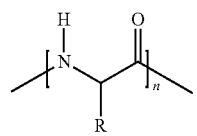

in Chemical Formula 2, 2a, 2b, 2c, or 2d may be a peptide wherein identical or different amino acid residues selected from the group consisting of glycine, lysine, histidine, serine, proline, hydroxyproline, threonine, arginine, glutamine, methionine, and glutamic acid are linked through amide bonding;

R is a side chain amino acid residue; and
n is an integer between 3 and 7.

More preferably, the peptide

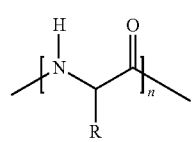

may be a tri-, tetra-, penta-, or hepta-peptide, with n being an integer between 3 and 6, particularly preferably one selected from the group consisting of glycine-lysine-histidine, glycine-histidine-lysine, glycine-proline-hydroxyproline, lysine-threonine-threonine-lysine-serine, and glutamic acid-glutamic acid-methionine-glutamine-arginine-arginine.

X in Chemical Formula 2 may be —OC(O)(CH$_2$)$_m$C(O)—, and m may be an integer between 2 and 4, more preferably 2 or 3.

Particularly preferably, X may be a succinyl group with m being 2.

In addition, —OC(O)(CH$_2$)$_p$CH$_3$ may be a fatty acid with p being an integer between 10 and 20, more preferably an integer between 12 and 16. Particularly preferably, it may be a palmitate with p being 14.

In a preferred embodiments of the present invention, the stabilized vitamin C derivative represented by Chemical Formula 1 or 2 may be one selected from the group consisting of 2-tetramethylphosphorodiamidic-5-(succinyl-lysine-threonine-threonine-lysine-serine) ascorbic acid, 2-tetramethylphosphorodiamidic-6-(succinyl-lysine-threonine-threonine-lysine-serine) ascorbic acid, 2-phospho-5-(succinyl-lysine-threonine-threonine-lysine-serine) ascorbic acid, 2-phospho-6-(succinyl-lysine-threonine-threonine-lysine-serine) ascorbic acid, 2-tetramethylphosphorodiamidic-5-(succinyl-glycine-lysine-histidine) ascorbic acid, 2-tetramethylphosphorodiamidic-6-(succinyl-glycine-lysine-histidine) ascorbic acid, 2-phospho-5-(succinyl-glycine-lysine-histidine) ascorbic acid, 2-phospho-6-(succinyl-glycine-lysine-histidine) ascorbic acid, 2-tetramethylphosphorodiamidic-5-(succinyl-glycine-histidine-lysine) ascorbic acid, 2-tetramethylphosphorodiamidic-6-(succinyl-glycine-histidine-lysine) ascorbic acid, 2-phospho-5-(succinyl-glycine-histidine-lysine) ascorbic acid, 2-phospho-6-(succinyl-glycine-histidine-lysine) ascorbic acid, 2-tetramethylphosphorodiamidic-5-(succinyl-glycine-proline-hydroxyproline) ascorbic acid, 2-tetramethylphosphorodiamidic-6-(succinyl-glycine-proline-hydroxyproline) ascorbic acid, 2-phospho-5-(succinyl-glycine-proline-hydroxyproline) ascorbic acid, 2-phospho-6-(succinyl-glycine-proline-hydroxyproline) ascorbic acid, 2-tetramethylphosphorodiamidic-5-(succinyl-glutamic acid-glutamic acid-methionine-glutamine-arginine-arginine) ascorbic acid, 2-tetramethylphosphorodiamidic-6-(succinyl-glutamic acid-glutamic acid-methionine-glutamine-arginine-arginine) ascorbic acid, 2-phospho-5-(succinyl-glutamic acid-glutamic acid-methionine-glutamine-arginine-arginine) ascorbic acid, 2-phospho-6-(succinyl-glutamic acid-glutamic acid-methionine-glutamine-arginine-arginine) ascorbic acid, 2-tetramethyl phosphorodiamidic-5-(succinyl-lysine-threonine-threonine-lysine-serine)-6-palmithyl ascorbic acid, 2-tetramethylphosphorodiamidic-5-palmithyl-6-(succinyklysine-threonine-threonine-lysine-serine) ascorbic acid, 2-phospho-5-(succinyl-lysine-threonine-threonine-lysine-serine)-6-palmithyl ascorbic acid, 2-phospho-5-palmithyl-6-(succinyl-lysine-threonine-threonine-lysine-serine) ascorbic acid, 2-tetramethylphosphorodiamidic-5-(succinyl-glycine-lysine-histidine)-6-palmithyl ascorbic acid, 2-tetramethylphosphorodiamidic-5-palmithyl-6-(succinyl-glycine-lysine-histidine) ascorbic acid, 2-phospho-5-(succinyl-glycine-lysine-histidine)-6-palmithyl ascorbic acid, 2-phospho-5-palmithyl-6-(succinyl-glycine-lysine-histidine) ascorbic acid, 2-tetramethylphosphorodiamidic-5-(succinyl-glycine-histidine-lysine)-6-palmithyl ascorbic acid, 2-tetramethylphosphorodiamidic-5-palmithyl-6-(succinyl-glycine-histidine-lysine) ascorbic acid, 2-phospho-5-(succinyl-glycine-histidine-lysine)-6-palmithyl ascorbic acid, 2-phospho-5-palmithyl-6-(succinyl-glycine-histidine-lysine) ascorbic acid, 2-tetramethylphosphorodiamidic-5-(succinyl-glycine-proline-hydroxyproline)-6-palmithyl ascorbic acid, 2-tetramethylphosphorodiamidic-5-palmithyl-6-(succinyl-glycine-proline-hydroxyproline) ascorbic acid, 2-phospho-5-(succinyl-glycine-proline-hydroxyproline)-6-palmithyl ascorbic acid, 2-phospho-5-palmithyl-6-(succinyl-glycine-proline-hydroxyproline) ascorbic acid, 2-tetramethylphosphorodiamidic-5-(succinyl-glutamic acid-glutamic acid-methionine-glutamine-arginine-arginine)-6-palmithyl ascorbic acid, 2-tetramethylphosphorodiamidic-5-palmithyl-6-(succinyl-glutamic acid-glutamic acid-methionine-glutamine-arginine-arginine) ascorbic acid, 2-phospho-5-(succinyl-glutamic acid-glutamic acid-methionine-glutamine-arginine-arginine)-6-palmithyl ascorbic acid, 2-phospho-5-palmithyl-6-(succinyl-glutamic acid-glutamic acid-methionine-glutamine-arginine-arginine) ascorbic acid, and pharmaceutically acceptable salts thereof.

In the most preferred embodiment of the present invention, the stabilized vitamin C derivative represented by Chemical Formula 1 or 2 may be one selected from the group consisting of 2-tetramethylphosphorodiamidic-5-(succinyl-lysine-threonine-threonine-lysine-serine) ascorbic acid, 2-phospho-5-(succinyl-lysine-threonine-threonine-lysine-serine) ascorbic acid, 2-tetramethylphosphorodiamidic-5-(succinyl-glycine-lysine-histidine) ascorbic acid, 2-phospho-5-(succinyl-glycine-lysine-histidine) ascorbic acid, 2-tetramethylphosphorodiamidic-5-(succinyl-glycine-histidine-lysine) ascorbic acid, 2-phospho-5-(succinyl-glycine-histidine-lysine) ascorbic acid, 2-tetramethylphosphorodiamidic-5-(succinyl-glycine-proline-hydroxyproline) ascorbic acid, 2-phospho-5-(succinyl-glycine-proline-hydroxyproline) ascorbic acid, 2-tetramethylphosphorodiamidic-5-(succinyl-glutamic acid-glutamic acid-methionine-glutamine-arginine-arginine) ascorbic acid, 2-phospho-5-(succinyl-glutamic acid-glutamic acid-methionine-glutamine-arginine-arginine) ascorbic acid, 2-tetramethylphosphorodiamidic-5-palmithyl-6-(succinyl-lysine-threonine-threonine-lysine-serine) ascorbic acid, 2-phospho-5-palmithyl-6-(succinyl-lysine-threonine-threonine-lysine-serine) ascorbic acid, 2-tetramethylphosphorodiamidic-5-palmithyl-6-(succinyl-glycine-lysine-histidine) ascorbic acid, 2-phospho-5-palmithyl-6-(succinyl-glycine-lysine-histidine) ascorbic acid, 2-tetramethylphosphorodiamidic-5-palmithyl-6-(succinyl-glycine-histidine-lysine) ascorbic acid, 2-phospho-5-palmithyl-6-(succinyl-glycine-histidine-lysine) ascorbic acid, 2-tetramethylphosphorodiamidic-5-palmithyl-6-(succinyl-glycine-proline-hydroxyproline) ascorbic acid, 2-phospho-5-palmithyl-6-(succinyl-glycine-proline-hydroxyproline) ascorbic acid, 2-tetramethylphosphorodiamidic-5-palmithyl-6-(succinyl-glutamic acid-glutamic acid-methionine-glutamine-arginine-arginine) ascorbic acid, 2-phospho-5-palmithyl-6-(succinyl-glutamic acid-glutamic acid-methionine-glutamine-arginine-arginine) ascorbic acid, and pharmaceutically acceptable salts thereof.

In this description, the "natural peptide" refers to a peptide having α-amino acids selected from the group consisting of alanine, valine, leucine, isoleucine, proline, phenylalanine, tryptophan, methionine, glycine, serine, threonine, cysteine, tyrosine, asparagine, glutamine, lysine, arginine, histidine, aspartic acid, and glutamic acid. And, the "non-natural peptide" refers to a peptide having amino acids not encoded by a nucleic acid codon. It includes, for example, D-isomers of the above natural α-amino acids; Aib (aminobutyric acid), bAib (3-aminoisobutyric acid), Nva (norvaline), β-Ala, Aad (2-aminoadipic acid), bAad (3-aminoadipic acid), Abu (2-aminobutyric acid), Gaba (γ-aminobutyric acid), Acp (6-aminocaproic acid), Dbu (2,4-diaminobutyric acid), α-aminopimelic acid, TMSA (trimethylsilyl-Ala), alle(allo-isoleucine), Nle (norleucine), tert-Leu, Cit (citrulline), Orn, Dpm (2,2'-diaminopimelic acid), Dpr (2,3-diaminopropionic acid), α- or β-Nal, Cha (cyclohexyl-Ala), hydroxyproline, Sar (sarcosine), etc.; cyclic amino acids; N-α-alkylated amino acids, e.g., MeGly (N-α-methylglycine), EtGly (N-α-ethylglycine), and EtAsn(N-α-ethylasparagine); and amino acids with two side chain substituents at the α-carbon, etc.

As used herein, the term "peptide" refers to a polymer made up of 10 or less (preferably 3 to 10) amino acid residues linked through amide bonds (or peptide bonds). The peptide may be one obtained by treating a protein extracted from the body with a protease, or one synthesized by a gene recombination and protein expression system. Preferably, the peptide may be synthesized in vitro using a peptide synthesizer, etc. The peptide may be a derivative with a particular atom or atom group substituted by a hydroxyl group, etc. Hereinbelow, the COOH terminus of a peptide is abbreviated as C-terminus, and the $NH_2$ terminus as N-terminus.

In the present invention, the peptide may particularly include a collagen-producing peptide. The "collagen-producing peptide" refers to a fragment of a collagen protein, which can be utilized to promote the synthesis of collagen or can be used as a constituent of collagen. For example, a tri-, tetra-, penta-, or hepta-peptide selected from the group consisting glycine-lysine-histidine, glycine-histidine-lysine, glycine-proline-hydroxyproline, lysine-threonine-threonine-lysine-serine, and glutamic acid-glutamic acid-methionine-glutamine-arginine-arginine, which may be used in an embodiment of the present invention, promotes the synthesis of collagen and glycosaminoglycan in the dermis, thereby increasing moisture retention ability and elasticity of the dermis and improving wrinkle problems. Particularly, the pentapeptide lysine-threonine-threonine-lysine-serine is the C-terminal fragment of collagen type I, which is important with regard to skin connective tissues, wrinkle formation, and moisturization. It is reported that the peptide promotes the synthesis of fibronectin, which helps intercellular communication between collagen types I and III and between cells during the cell culturing of fibroblasts that produce collagen, and the synthesis of the growth factor β-TGF (Kou Katayama et al., 1991, Biochemistry 30: 7097-7104) and promotes its transcription by binding to the collagen gene promoter (Kou Katayama et al., 1993, *The Journal of Biological Chemistry* 268(14): 9941-9944).

As used herein, the "pharmaceutically acceptable salt" includes salts derived from a pharmaceutically acceptable inorganic acid, organic acid, or base. Examples of salts derived from pharmaceutically acceptable acids may be selected from the group consisting of hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples salts derived form of pharmaceutically acceptable bases are alkali metals such as sodium, etc., alkaline earth metals such as magnesium, etc., ammonium, etc.

As used herein, "ascorbic acid" has the same meaning as "vitamin C."

The vitamin C derivative of the present invention has been invented to solve the low stability problem of conventional vitamin C, in spite of superior antioxidant activity, skin whitening, and regeneration ability, etc. The stability is improved by introducing a phosphate derivative or glucose at the C-2 position of vitamin C, and is further improved by introducing a particular peptide at the C-5 or C-6 position. Particularly, if the peptide is a collagen-producing peptide, a skin condition improvement effect, including wrinkle improvement, skin elasticity improvement, etc., can be attained additionally by collagen.

In still another aspect, the present invention provides a method of preparing a stabilized vitamin C derivative comprising the steps of:

introducing a phosphoryl group, a phosphate derivative or glucose at the C-2 position of vitamin C to substitute for hydroxyl group at C-2 position of vitamin C; and introducing —OH or a fatty acid ester having 12 to 22 carbon atoms at one of C-5 and C-6 positions, and introducing a peptide having 3 to 10 amino acid residues at the other position.

In an embodiment of the present invention, the preparation method of a stabilized vitamin C derivative of the present invention may be a method of preparing the vitamin C derivative with a peptide molecule represented by Chemical Formula 1, or a pharmaceutically acceptable salt thereof, which comprises the steps of:

introducing glucose, a phosphoryl group or a phosphate derivative represented by the following Chemical Formula 6 to substitute for the hydroxyl group at the C-2 position of vitamin C (the step of introducing a benzyl or other protecting group to the hydroxyl group of the C-3 position may be optionally included, if required);

generating a hydroxyl group at one of the C-5 and C-6 positions of vitamin C and a dicarboxylic acid $HOOC(CH_2)_m COOH$ (m is an integer between 2 and 5) at the other position through an ester bond; and linking a peptide having 3 to 10 amino acid residues to the dicarboxylic acid through an amide bond.

In an embodiment of the present invention, the preparation method of the vitamin C derivative represented by Chemical Formula 1 may include, but not be limited to, the steps of:

reacting the 5,6-isopropylidene-ascorbic acid represented by the following Chemical Formula 3 with a benzyl halide represented by the following Chemical Formula 4 to introduce a benzyl group at the hydroxyl group of the C-3 position of 5,6-isopropylidene-ascorbic acid and obtain the benzyl-substituted 5,6-isopropylidene-ascorbic acid represented by the following Chemical Formula 5;

reacting the ascorbic acid derivative represented by Chemical Formula 5 with a phosphorodiamidic halide represented by the following Chemical Formula 6 to introduce a phosphorodiamide group at the hydroxyl group of the C-2 position and obtain the benzyl- and phosphorodiamide-substituted 5,6-isopropylidene-ascorbic acid represented by the following Chemical Formula 7; opening the ring of the ascorbic acid derivative represented by Chemical Formula 7, and generating a hydroxyl group at one of the C-5 and C-6 positions and introducing a dicarboxylic acid represented by the following Chemical Formula 8 to obtain the ascorbic acid derivative bonded with the dicarboxylic acid through ester bonding, which is represented by the following Chemical Formula 9;

linking the ascorbic acid derivative represented by Chemical Formula 9 with a peptide represented by the following Chemical Formula 10 through amide bonding; and removing the benzyl group:

(Chemical Formula 3)

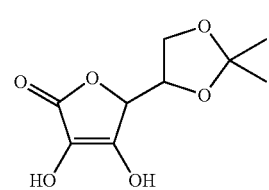

(Chemical Formula 4)

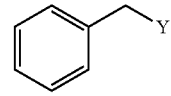

-continued

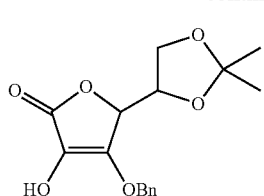
(Chemical Formula 5)

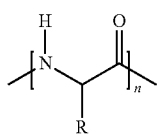
(Chemical Formula 6)

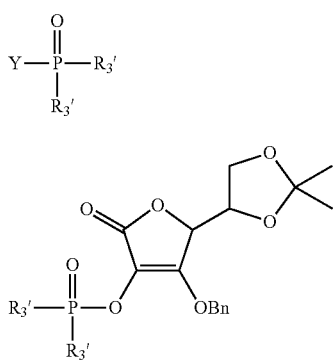
(Chemical Formula 7)

HOOC(CH$_2$)$_m$COOH
(Chemical Formula 8)

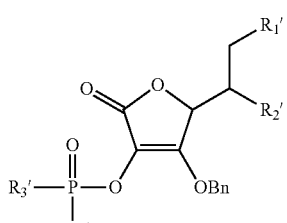
(Chemical Formula 9)

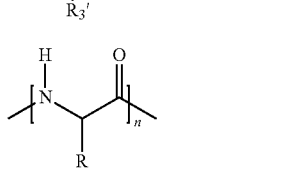
(Chemical Formula 10)

wherein
m is an integer between 2 and 5;
Bn is benzyl;
Y is chlorine, bromine, fluorine, or iodine;
R3' is dimethylamine, diethylamine, propylamine, or benzylamine;
R1' and R2' are —OH or —OC(O)(CH$_2$)mC(O)OH, and are different from each other, wherein they are not simultaneously —OH or —OC(O)(CH$_2$)mC(O)OH;
R is a protected or unprotected side chain of a natural or non-natural amino acid residue; and
n is an integer between 3 and 10.

In a more preferred embodiment, the vitamin C derivative represented by Chemical Formula 1 and a pharmaceutically acceptable salt thereof may be prepared as follows.

First, a benzyl halide represented by Chemical Formula 4, preferably benzyl chloride (Y=chlorine), is added to the 5,6-isopropylidiene-ascorbic acid represented by Chemical Formula 3 and reaction is performed for 3 to 5 hours, preferably for 4 hours, at 4 to 50° C., preferably at 20 to 30° C., particularly preferably at 25° C., to introduce the benzyl group at the hydroxyl group of the C-3 position of ascorbic acid (vitamin C). Subsequently, a phosphorodiamidic halide represented by Chemical Formula 6, preferably N,N,N',N'-tetramethylphosphorodiamidic chloride, is added to the benzyl-substituted compound represented by Chemical Formula 5, in which the benzyl group is introduced at the hydroxyl group of the C-3 position, and reaction is performed for 5 to 7 hours, preferably for 6 hours, at 4 to 70° C., preferably at 20 to 30° C., particularly preferably at 25° C., to obtain the compound represented by Chemical Formula 7, in which the benzyl group is introduced at the hydroxyl group of the C-3 position of ascorbic acid and the N,N,N',N'-tetramethylphosphorodiamide group is introduced at the C-2 position.

To the resultant compound, an acid, preferably trifluoroacetic acid, is added and reaction is performed for 3 to 5 hours, preferably for 4 hours, to open the 5,6-isopropylidiene ring. Subsequently, a dicarboxylic acid represented by Chemical Formula 8, preferably succinic acid, is added and reaction is performed for 15 to 17 hours, preferably for 16 hours, at 4 to 70° C., preferably at 20 to 30° C., particularly preferably at 25° C., with ascorbic acid to form the compound represented by Chemical Formula 9 through ester bonding. Then, the protected NH$_2$ group of the N-terminus is linked with the dicarboxylic acid through amide bonding by the conventional solid phase synthesis in resin, and the protecting group is removed (deprotection).

The reaction may be performed under an anhydrous condition, for example by using an anhydrous organic solvent. For the anhydrous organic solvent, any commonly used anhydrous organic solvent, e.g., dimethylformamide, dimethylsulfoxide, N-methylpyrrolidinone, dichloromethane, etc., preferably dimethylformamide, may be used. In addition, a condensing agent, for example DCC(N,N'-dicyclohexylcarbodiimide), HOBT (N-hydroxybenzotriazole), EDC [N-(3-dimethylaminopropyl)-N'-ethyl-carbodiimide], PyBOP (benzotriazole-1-yl-oxy-tris-pyrrolidinophosphonium hexafluorophosphate), HBTU [2-(1H-benzotriazole-1-yl)-1,3,3-tetramethyluronium hexafluorophosphate], etc. may be used in the reaction.

In another embodiment of the present invention, the preparation method of a stabilized vitamin C derivative of the present invention may be a preparation method of the stabilized vitamin C derivative with a peptide molecule represented by Chemical Formula 2 or a pharmaceutically acceptable salt thereof, which includes the steps of:

introducing glucose, a phosphoryl group, or a phosphate derivative represented by the following Chemical Formula 6 at the hydroxyl group of the C-2 position of vitamin C (the step of introducing a benzyl group or other protecting group to the hydroxyl group of the C-3 position may be further added, if required); and introducing a fatty acid ester having 12 to 22 carbon atoms to the hydroxyl group of any one of C-5 and C-6 positions of vitamin C and introducing the dicarboxylic acid HOOC(CH$_2$)$_m$COOH (m is an integer between 2 and 5) at the other hydroxyl group through ester bonding and linking with a peptide having 3 to 10 amino acid residues through amide bonding.

In an embodiment of the present invention, the preparation method of the vitamin C derivative represented by Chemical Formula 2 or a pharmaceutically acceptable salt thereof comprises the steps of:

reacting the 5,6-isopropylidiene-ascorbic acid represented by Chemical Formula 3 with a benzyl halide represented by the following Chemical Formula 4 to introduce the benzyl group at the hydroxyl group of the C-3 position of the 5,6-isopropylidiene-ascorbic acid and obtain the 5,6-isopropylidiene-ascorbic acid represented by the following Chemical Formula 5;

reacting the ascorbic acid derivative represented by Chemical Formula 5 with a phosphorodiamidic halide represented by the following Chemical Formula 6 to introduce the phosphorodiamide group at the hydroxyl group of the C-2 position and obtain the 5,6-isopropylidiene-ascorbic acid represented by the following Chemical Formula 7, which is substituted with the benzyl group and the phosphorodiamide group;

opening the ring of the ascorbic acid derivative represented by Chemical Formula 7, reacting the hydroxyl group of any one of the C-5 and C-6 positions with a fatty acid represented by the following Chemical Formula 11 and reacting the other hydroxyl group with dicarboxylic acid represented by the following Chemical Formula 8 to obtain the ascorbic acid derivative represented by the following Chemical Formula 12, which is bound to the fatty acid and the dicarboxylic acid through ester bonding;

reacting the resultant ascorbic acid derivative represented by Chemical Formula 9 with a peptide represented by the following Chemical Formula 10 to form an amide bonding with the dicarboxylic acid; and removing the benzyl group:

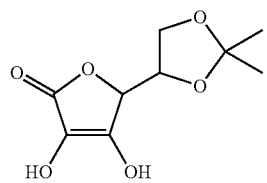
(Chemical Formula 3)

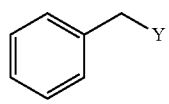
(Chemical Formula 4)

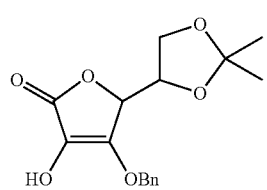
(Chemical Formula 5)

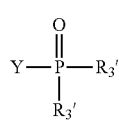
(Chemical Formula 6)

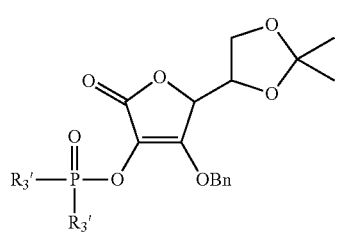
(Chemical Formula 7)

HOOC(CH$_2$)$_m$COOH
(Chemical Formula 8)

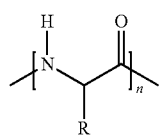
(Chemical Formula 10)

CH$_3$(CH$_2$)$_p$COOH
(Chemical Formula 11)

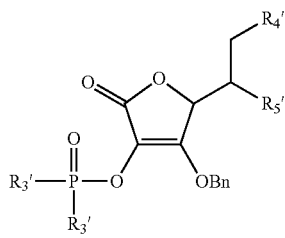
(Chemical Formula 12)

wherein
m is an integer between 2 and 5;
Bn is benzyl;
Y is chlorine, bromine, fluorine, or iodine;
R3' is dimethylamine, diethylamine, propylamine, or benzylamine;
R4' R5' are —OC(O)(CH$_2$)pCH$_3$ or —OC(O)(CH$_2$)mC(O)OH, and are different from each other, wherein they are not simultaneously —OC(O)(CH$_2$)pCH$_3$ or —OC(O)(CH$_2$)mC(O)OH;
R is a protected or unprotected side chain of a natural or non-natural amino acid residue;
n is an integer between 3 and 10; and
p is an integer between 10 and 20.

In a more preferred embodiment, the vitamin C derivative represented by Chemical Formula 2 or a pharmaceutically acceptable salt thereof may be prepared as follows.

First, a benzyl halide represented by Chemical Formula 4, preferably benzyl chloride (Y=chlorine), is added to the ascorbic acid derivative represented by Chemical Formula 3 and reaction is performed for 3 to 5 hours, preferably for 4 hours, at 4 to 70° C., preferably at 20 to 30° C., particularly preferably at 25° C. to obtain the ascorbic acid derivative represented by Chemical Formula 5, in which the hydroxyl group of the C-3 position of ascorbic acid is substituted by the benzyl group. A phosphorodiamidic halide, preferably N,N,N',N'-tetramethylphosphorodiamidic chloride, is added to the resultant ascorbic acid derivative and reaction is performed for 5 to 7 hours, preferably for 6 hours, at 4 to 70° C., preferably at 20 to 30° C., particularly preferably at 25° C., to obtain the ascorbic acid derivative represented by Chemical Formula 7, in which the benzyl group is introduced at the hydroxyl group of the C-3 position of ascorbic acid and the N,N,N',N'-tetramethylphosphorodiamide is introduced at the hydroxyl group of the C-2 position. An acid, preferably trifluoroacetic acid, is added to the resultant ascorbic acid derivative and reaction is performed for 3 to 5 hours, preferably for 4 hours, to open the 5,6-isopropylidiene ring. Then, a fatty acid represented by Chemical Formula 11, preferably palmitic acid, is added and reaction is performed for 15 to 17 hours, preferably for 16 hours, at 4 to 70° C., preferably at 20 to 30° C., particularly preferably at 25° C., to link with the hydroxyl group of the C-5 or C-6 position of the ring-opened ascorbic acid derivative through ester bonding. Subsequently, a dicarboxylic acid represented by Chemical Formula 8, preferably succinic acid, is added and reaction is performed for 15 to 17 hours, preferably for 16 hours, at 4 to 70° C., preferably at 20 to 30° C., particularly preferably at 25° C., to link the hydroxyl group of the C-5 or C-6 position of the ring-opened ascorbic acid not bonded to the fatty acid through ester bonding to obtain the ascorbic acid derivative represented by Chemical Formula 12. The protected NH$_2$ group of the N-terminus of the resultant ascorbic acid derivative is linked with the dicarboxylic acid through amide bonding by the conventional solid phase synthesis in resin and deprotection is performed.

The reaction may be performed under an anhydrous condition, for example, using an anhydrous organic solvent. The anhydrous organic solvent may be any commonly used anhydrous organic solvent, e.g., dimethylformamide, dimethylsulfoxide, N-methylpyrrolidinone, dichloromethane, etc., preferably dimethylformamide. In addition, a condensing agent, e.g., DCC(N,N'-dicyclohexylcarbodiimide), HOBT (N-hydroxybenzotriazole), EDC [N-(3-dimethylaminopropyl)-N'-ethyl-carbodiimide], PyBOP (benzotriazole-1-yl-oxy-tris-pyrrolidinophosphonium hexafluorophosphate), HBTU [2-(1 H-benzotriazole-1-yl)-1,3,3-tetramethyluronium hexafluorophosphate], etc., may be used during the reaction.

In the present invention, any condensing agent, catalyst, solvent, etc., commonly used in the related field may be used, so long as it does not negatively affect the reaction.

The obtained stabilized vitamin C derivative with a peptide molecule of the present invention represented by Chemical Formula 1 or 2 may be purified by the conventional separation and purification method, for example by recrystallization or column chromatography.

In the preparation method of the compound represented by Chemical Formula 1 or 2 in accordance with the present invention, the peptide that is linked with the ascorbic acid whose hydroxyl group is protected with the benzyl group may be prepared by solid phase synthesis. For example, after protecting each of the hydroxyl groups of ascorbic acid, a succinyl group is selectively introduced to the unprotected hydroxyl group. Then, the succinyl-substituted ascorbic acid is reacted with a peptide prepared by solid phase synthesis in resin at the N-terminus of the peptide, and the protecting groups are removed from the ascorbic acid and the peptide.

The following schemes are examples of the preparation method of the vitamin C derivative compound represented by Chemical Formula 1 or 2 in solid phase or solution phase. Scheme 1 is a process for preparing the compounds represented by Chemical Formulae 1a and 1c, Scheme 2 is a process for preparing the compounds represented by Chemical Formulae 1b and 1d, Scheme 3 is a process for preparing the compounds represented by Chemical Formulae 2b and 2d, and Scheme 4 is the process for preparing the compounds represented by Chemical Formulae 2a and 2c.

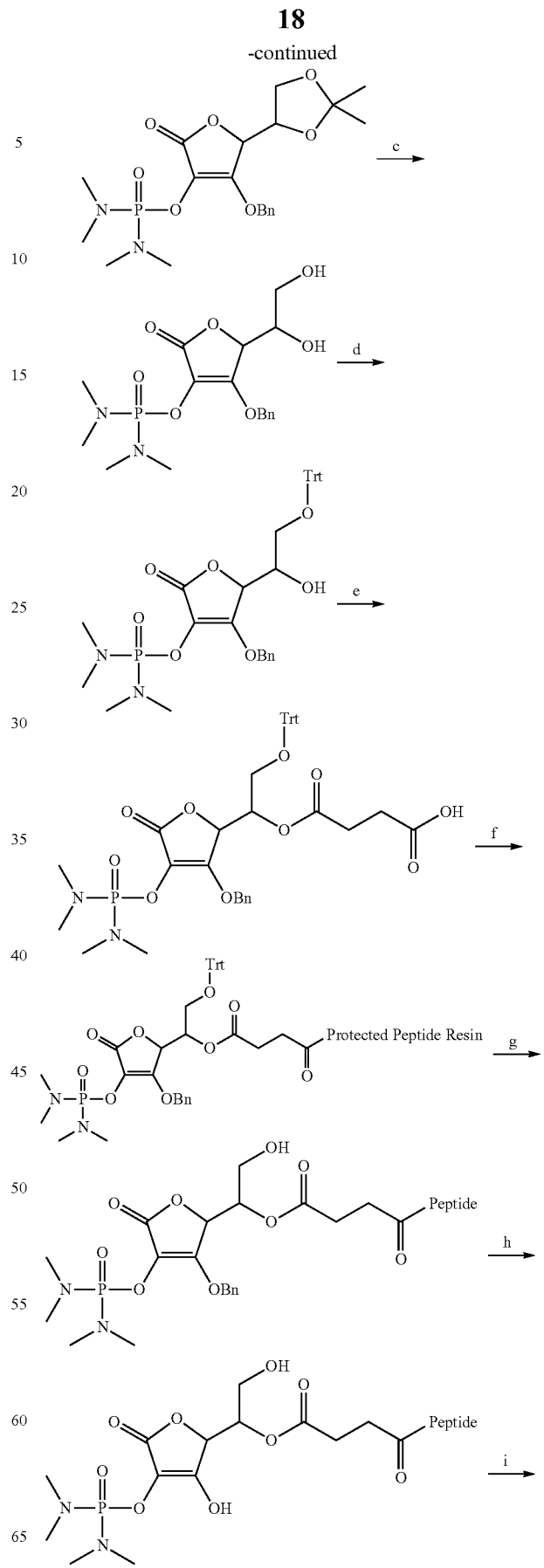

19

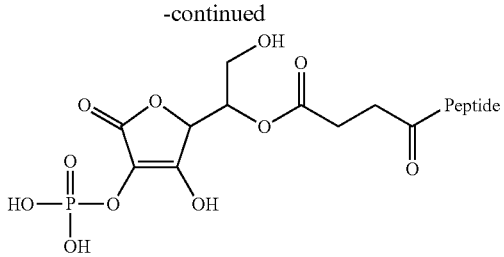

a: BnCl, K₂CO₃, DMF, 25° C., 4 hr
b: P(O)N(CH₃)₂Cl, DMAP, DCM, 25° C., 6 hr
c: TFA, DCM, 26° C., 4 hr
d: TrtCl, TEA, DCM, 25° C., 24 hr
e: Succinic anhydride, DMAP, DCM, 25° C., 16 hr
f: Solid phase synthesis
g: TFA, 25° C., 3 hr
h: 10% Pd/C, MeOH, H₂, 25° C., 1 hr
i: Dowex 50w-8x, H₂O, 25° C., 24 hr
(BnCl: benzyl chloride; K₂CO₃: potassium carbonate; DMF: dimethylformamide; P(O)N(CH₃)₂Cl: tetramethylphosphorodiamidic chloride; DMAP: dimethyl-aminopyridine; TrtCl: triphenylmethyl chloride; TFA: trifluoroacetic acid; DCM: dichloromethane; TEA: triethylamine; MeOH: methanol; Dowex 50w-8x: cation exchange resin).

Scheme 2

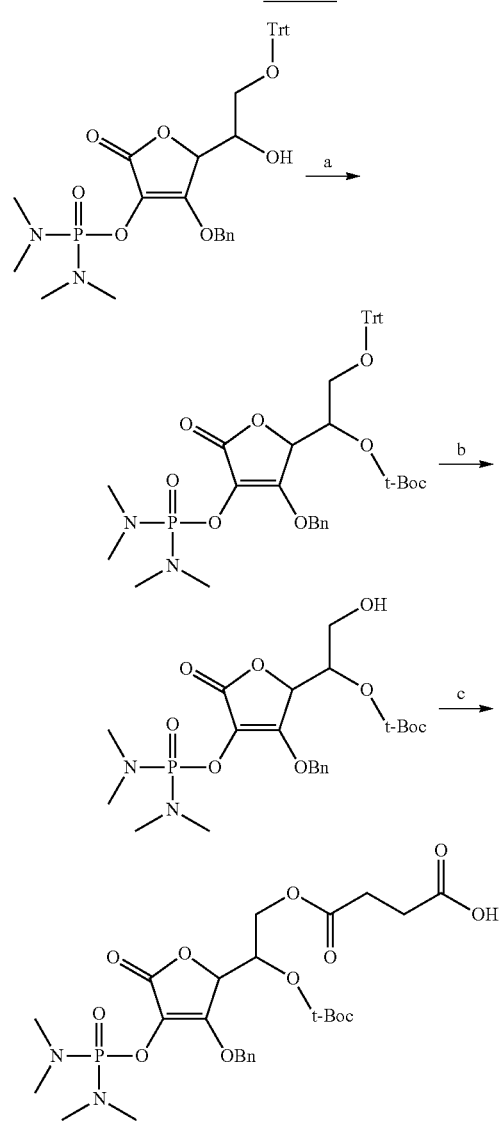

20

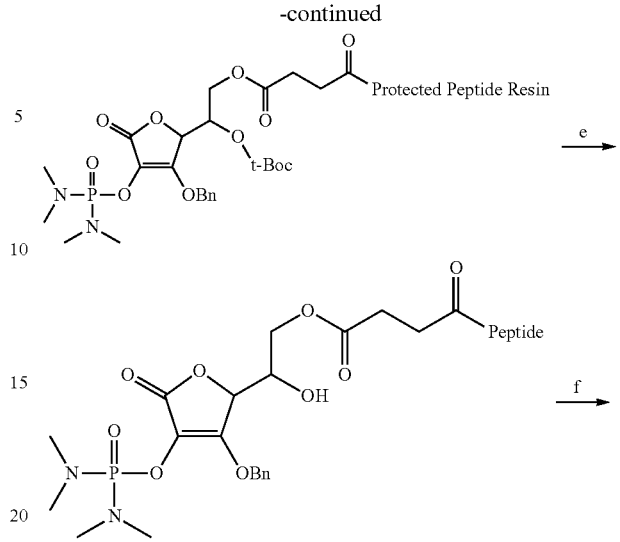

a: (t-Boc)₂O, TEA, DCM, 25° C., 12 hr
b: Dowex 50w-8x, MeOH, 60° C., 24 hr
c: Succinic anhydride, DMAP, DCM, 25° C., 16 hr
d: Solid phase synthesis
e: TFA, room temperature, 3 hr
f: 10% Pd/C, MeOH, H₂, 25° C., 1 hr
g: Dowex 50w-8x, H₂O, 25° C., 24 hr
((t-Boc)₂O: di-tert-butyl dicarbamate; TFA: trifluoroacetic acid; DCM: dichloromethane; TEA: triethylamine; MeOH: methanol; Dowex 50w-8x: cation exchange resin).

Scheme 3

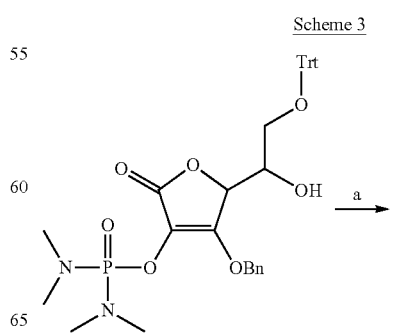

21
-continued
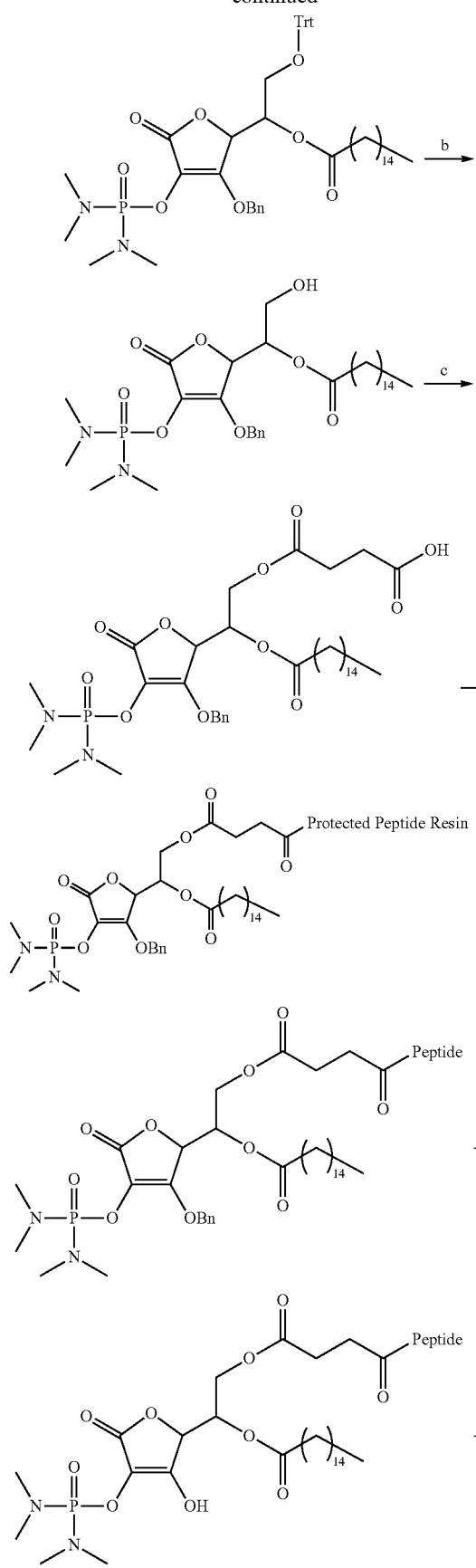
22
-continued
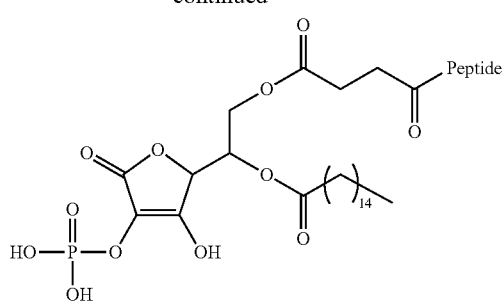
a: CH₃(CH₂)₁₄C(O)Cl, TEA, 25° C., 16 hr
b: Dowex 50w-8x, MeOH, 60° C., 24 hr
c: Succinic anhydride, DMAP, DCM, 25° C., 16 hr
d: Solid phase synthesis
e: TFA, room temperature, 3 hr
f: 10% Pd/C, MeOH, H₂, 25° C., 1 hr
g: Dowex 50w-8x, H₂O, 25° C., 24 hr
(CH₃(CH₂)₁₄C(O)Cl: palmitoyl chloride; TFA: trifluoroacetic acid; DCM: dichloromethane; TEA: triethylamine; MeOH: methanol; Dowex 50w-8x: cation exchange resin).
Scheme 4
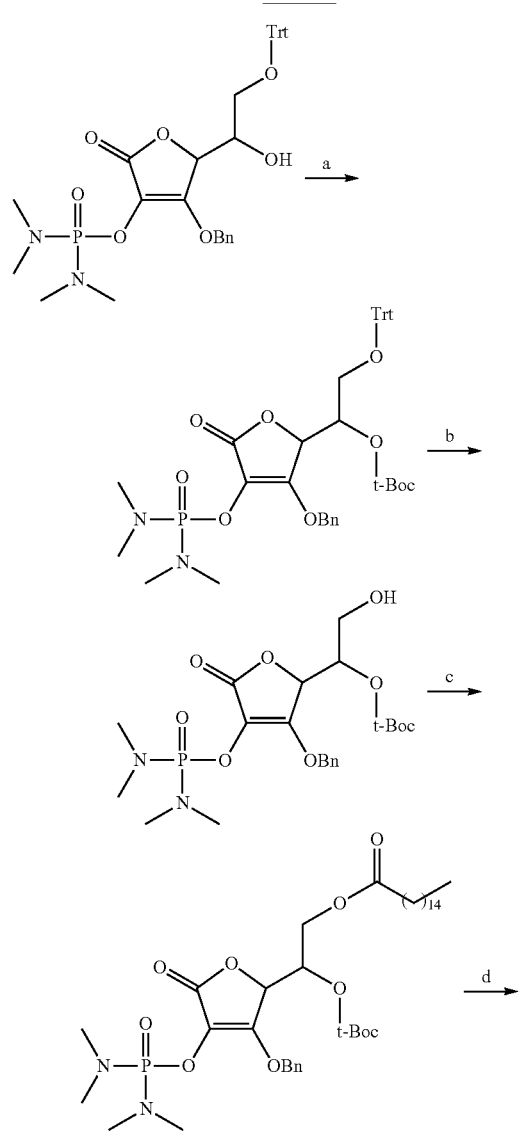

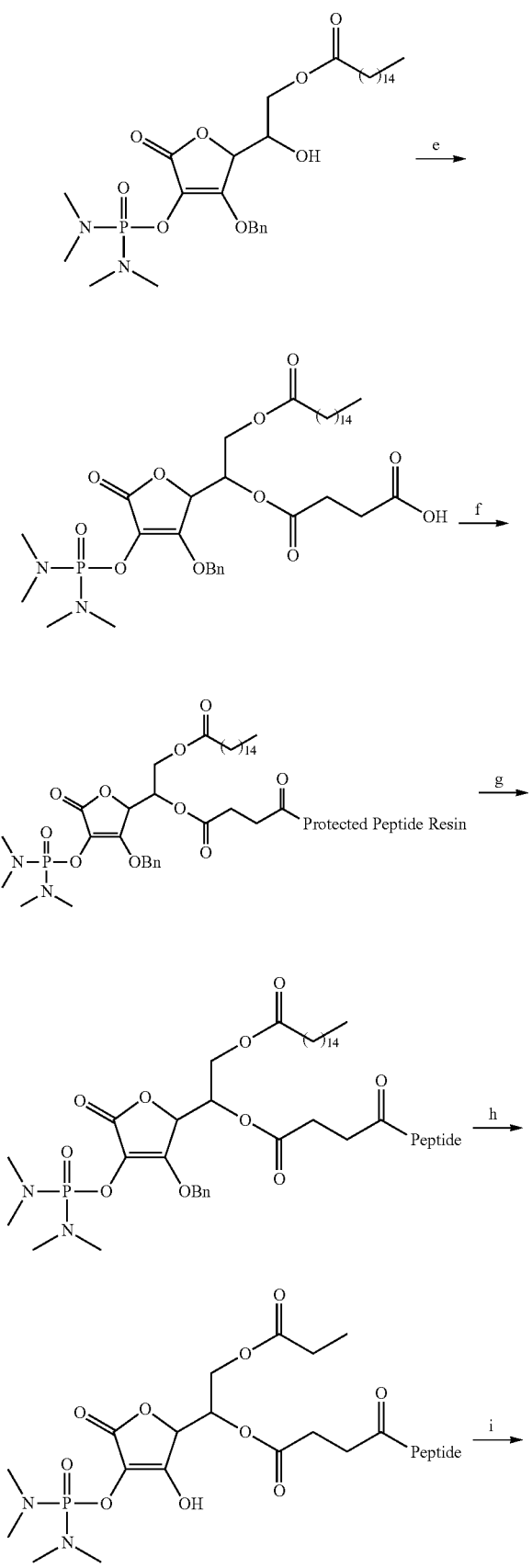

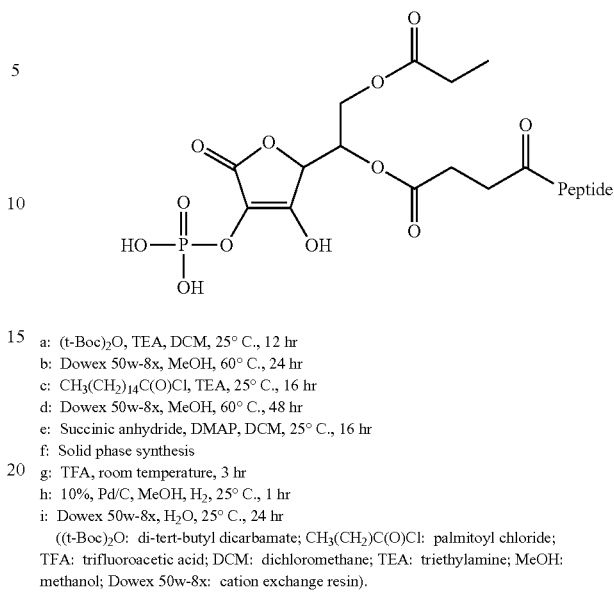

a: (t-Boc)$_2$O, TEA, DCM, 25° C., 12 hr
b: Dowex 50w-8x, MeOH, 60° C., 24 hr
c: CH$_3$(CH$_2$)$_{14}$C(O)Cl, TEA, 25° C., 16 hr
d: Dowex 50w-8x, MeOH, 60° C., 48 hr
e: Succinic anhydride, DMAP, DCM, 25° C., 16 hr
f: Solid phase synthesis
g: TFA, room temperature, 3 hr
h: 10%, Pd/C, MeOH, H$_2$, 25° C., 1 hr
i: Dowex 50w-8x, H$_2$O, 25° C., 24 hr
((t-Boc)$_2$O: di-tert-butyl dicarbamate; CH$_3$(CH$_2$)C(O)Cl: palmitoyl chloride; TFA: trifluoroacetic acid; DCM: dichloromethane; TEA: triethylamine; MeOH: methanol; Dowex 50w-8x: cation exchange resin).

In another aspect, the present invention provides an acylation agent including the compound represented by the following Chemical Formula 9 or 12, or a method of acylating a peptide or protein using the same:

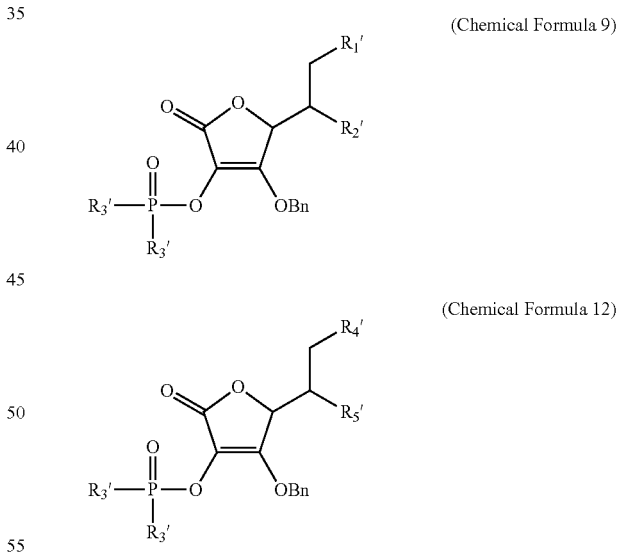

wherein

R3' is dimethylamine, diethylamine, propylamine, or benzylamine;

R1' and R2' are —OH, or —OC(O)(CH$_2$)mC(O)OH, and are different from each other, wherein they are not simultaneously —OH, or —OC(O)(CH$_2$)mC(O)OH; and R4' R5' are —OC(O)(CH$_2$)pCH$_3$ or —OC(O)(CH$_2$)mC(O)OH, and are different from each other, wherein they are not simultaneously —OC(O)(CH$_2$)pCH$_3$ or —OC(O)(CH$_2$)mC(O)OH.

As described above, the compound represented by Chemical Formula 9 or 12 may be used to acylate a compound having a functional group that can be substituted by the acyl group. For example, the compound represented by Chemical Formula 9 or 12 may be reacted with a compound having an amino group to form amide bonds. The compound having an amino group may be a peptide, as defined in this description, or a protein.

The stabilized vitamin C derivative with a peptide molecule of the present invention or a pharmaceutically acceptable salt thereof has superior antioxidation, antiaging, skin wrinkle improvement, and skin whitening effects without skin irritation, skin sensitization, phototoxicity, etc. in addition, since the vitamin C derivative of the present invention has lipophilicity similar to that of skin, it has superior skin permeability. When a collagen-producing peptide is bound, the vitamin C derivative may have a better skin wrinkle improvement effect. Further, since the vitamin C derivative of the present invention is bound to a phosphate derivative, it has significantly improved stability.

Thus, in another aspect, the present invention provides a composition for skin improvement including at least one selected from the group consisting of the compound represented by Chemical Formula 1, the compound represented by Chemical Formula 2, and pharmaceutically acceptable salts thereof as active ingredient. Preferably, the composition is used for skin application for transdermal administration. Because of the skin permeability and stability of the active ingredient, the composition is superior in offering the effects of skin anti-aging, wrinkle improvement, skin roughness improvement, skin whitening, skin moisturization, etc., and is thereby effective in improving skin conditions and preventing aggravation of skin conditions.

In this description, "for skin application" means that the composition is superior in offering the effects of skin moisturizing, skin whitening, wrinkle improvement, skin roughness improvement, promotion of transdermal absorption, etc., and thus, is used to improve skin conditions or to prevent aggravation of skin conditions. The preparation for skin application of the present invention may be used for cosmetics, medicine, and particularly for medicine for skin application such as ointments, etc. Preferably, it is used for cosmetics, without any particular limitation in the form.

In the composition in accordance with the present invention, the content of the active ingredient, or the at least one substance selected from the group consisting of the compound represented by Chemical Formula 1, the compound represented by Chemical Formula 2, and pharmaceutically acceptable salts thereof, can be determined adequately, considering the use, form, purpose, etc., of the composition. A content of at least 0.001% is preferable, because a substantial skin improvement effect cannot be expected with a content smaller than 0.001%. In a preferred embodiment of the present invention, the composition for skin improvement of the present invention may comprise the active ingredient at 0.001 to 50% (w/w), preferably at 0.001 to 5% (w/w), and more preferably at 0.01 to 3% (w/w).

In addition, the composition for skin improvement of the present invention may include a commonly used solvent, for example at least one selected from the group consisting of ethanol, glycerin, butylene glycol, propylene glycol, Glycereth-26, Methylgluceth-20, isocetyl myristate, isocetyl octanoate, octyldodecyl myristate, octyldodecanol, isostearyl isostearate, cetyl octanoate, and neopentyl glycol dicaprate. When the composition of the present invention is prepared using these solvents, the solubility of the compound varies slightly, depending on the particular compound and the mixing ratio of the solvents. However, those skilled in the art can select the particular solvent to be used and its content adequately, depending on the characteristics of the product.

Further, the composition for skin improvement of the present invention may include an adequate additive such as perfume, pigment, antiseptic, vehicle, etc., depending on the form of the composition.

The composition for skin improvement of the present invention may be prepared into a variety of product forms, including skin ointment, skin softener, nourishing lotion, nourishing cream, massage cream, essence, pack, etc. For example, when the composition is used for a skin ointment, it may include, in addition to the active ingredient, or the compound represented by Chemical Formula 1 or 2, 50.0-97.0 wt % of vaseline and 0.1-5.0 wt % of polyoxyethylene oleyl ether phosphate. When used for a skin softener, the composition may comprise 1.0-10.0 wt % of polyalcohol, such as propylene glycol, glycerin, etc., and 0.05-2.0 wt % of surfactant, such as polyethylene oleyl ether, polyoxyethylene hydrogenated castor oil, etc. Further, when used for a nourishing lotion or a nourishing cream, it may include, in addition to the active ingredient, 5.0-20.0 wt % of oil, such as squalene, Vaseline, and octyldodecanol, and 3.0-15.0 wt % of ethanol, stearyl alcohol, beeswax, etc. When used for an essence, it may include 5.0-30.0 wt % of polyalcohol, such as glycerin, propylene glycol, etc. When used for a massage cream, the composition may include, in addition to the active ingredient, 30.0-70.0 wt % of an oil, such as liquid paraffin, vaseline, isononyl isononanoate, etc. And, when used for a pack, it may be prepared into a peel-off pack including 5.0-20.0 wt % of polyvinyl alcohol or a wash-off pack including general-purpose emulsion cosmetics and 5.0-30.0 wt % of pigment, such as kaolin, talc, zinc oxide, titanium dioxide, etc. Further, the composition for skin improvement of the present invention may include substances commonly used in general cosmetics, for example oil, water, a surfactant, a moisturizer, a low alcohol, a thickener, a chelating agent, a pigment, an antiseptic, a perfume, etc., as required.

In other aspect, the present invention provides a method of stabilizing vitamin C. The method may include the steps of:

introducing glucose or a phosphoryl group or a phosphate derivative represented by Chemical Formula 6 to substitute for a hydroxyl group at a C-2 position of vitamin C;

binding a peptide molecule having 3 to 10 amino acid residues selected from the group consisting of glycine, lysine, histidine, serine, proline, hydroxyproline, threonine, glutamic acid, methionine, glutamine, and arginine, to a C-5 or C-6 position of vitamin C through a dicarboxylic acid represented by the following Chemical Formula 8.

(Chemical Formula 6)

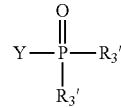

(Chemical Formula 8)

HOOC(CH$_2$)$m$COOH  (wherein Y and m are as the same as defined above).

The peptide molecule may be selected from glycine-histidine-lysine, glycine-lysine-histidine, glycine-proline-hydroxyproline, lysine-threonine-threonine-lysine-serine, and glutamic acid-glutamic acid-methionine-glutamine-arginine-arginine.

The present invention is further explained in more detail with reference to the following examples. These examples, however, should not be interpreted as limiting the scope of the present invention in any manner.

EXAMPLES

Example 1

Synthesis of 3-O-benzyl-2-O-tetramethylphosphorodiamidic-6-O-triphenylmethyl-5-O-succinyl-ascorbic acid 3-O-benzyl-2-O-tetramethylphosphorodiamidic-6-O-triphenylmethyl-5-O-succinyl-ascorbic acid was prepared by the following scheme.

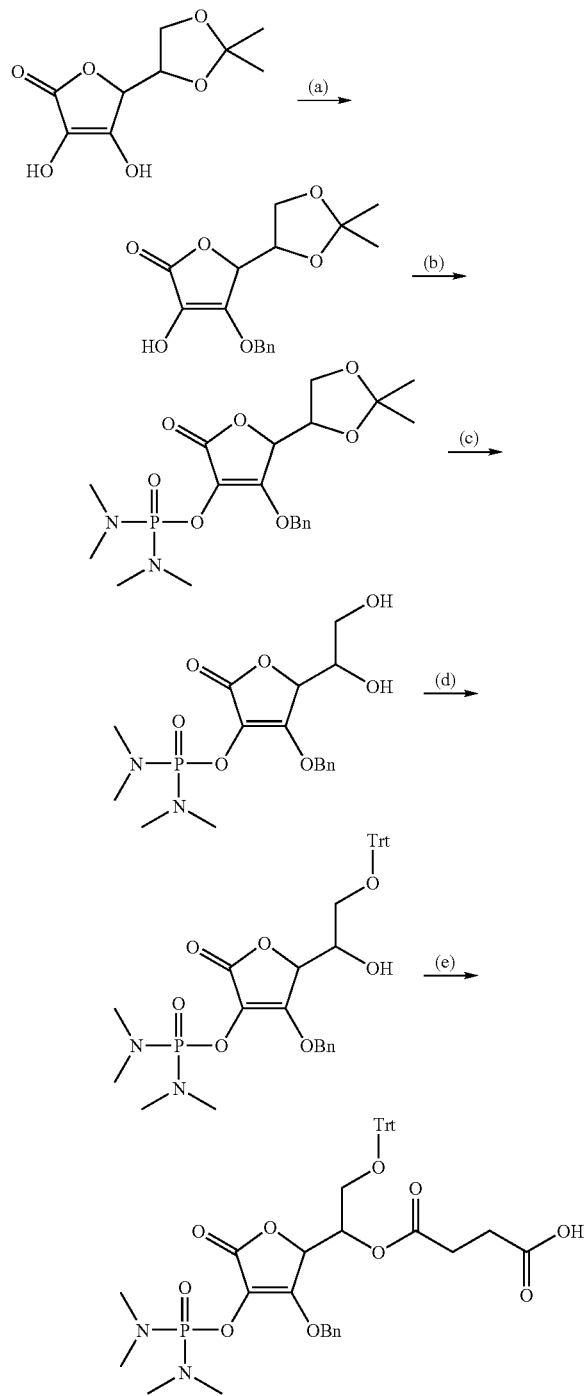

(a) Protection with Benzyl Group 5,6-Isopropylidiene-L-ascorbic acid (290 g, 1.34 mol) was dissolved in 2 L of dimethylformamide, and solid potassium carbonate (92.7 g, 0.67 mol) was added thereto. Benzyl chloride (115 g, 0.67 mmol) was added to the solution and stirring was performed at 25° C. for 4 hours. Dimethylformamide was removed from the solution under reduced pressure. The resultant solution was dissolved in 2 L of ethyl acetate and 2 L of water was added. The organic layer was extracted using a separatory funnel. This procedure was repeated 3 times to remove water-soluble impurities.

500 g of anhydrous sodium sulfate was added to the extracted organic layer to remove water. The remaining solution was concentrated under reduced pressure to obtain 300 g of 5,6-isopropylidiene-L-ascorbic acid in which the hydroxyl group at the C-3 position is protected by a benzyl group.

(b) Introduction of Phosphate Derivative 300 g of the obtained compound and 120 g of dimethylaminopyridine were dissolved in 2 L of dichloromethane. Then, 180 g of tetramethylphosphorodiamidic chloride was added, and stirring was performed at 25° C. for 6 hours. Dichloromethane was removed from the solution under reduced pressure. The resultant solution was dissolved in 2 L of ethyl acetate and 2 L of a 5% sodium hydrogen sulphate solution was added. The organic layer was extracted using a separatory funnel. 500 g of anhydrous sodium sulfate was added to the extracted organic layer to remove water. The remaining solution was concentrated under reduced pressure to obtain 300 g of 5,6-isopropylidiene-L-ascorbic acid in which tetramethylphosphorodiamide was introduced at the C-2 position.

(c) Ring Opening by Addition of Acid 300 g of the obtained compound was dissolved in 800 mL of dichloromethane and 200 mL of 20% (v/v) trifluoroacetic acid (TFA) was added. Stirring was performed at 25° C. for 4 hours. Dichloromethane and TFA were removed from the solution under reduced pressure and recrystallization was performed to obtain 250 g of a pale yellow, semi-solid, ring-opened ascorbic acid derivative.

(d) Protection of Hydroxyl Group at C-6 Position 250 g of the obtained compound and 64 g of triethylamine were dissolved in 1 L of dichloromethane and 180 g of triphenylmethyl chloride was added. Stirring was performed at 25° C. for 24 hours. Dichloromethane was removed from the solution under reduced pressure. The resultant solution was dissolved in 2 L of ethyl acetate and 2 L of a 5% sodium hydrogen sulphate solution was added. The organic layer was extracted using a separatory funnel. 500 g of anhydrous sodium sulfate was added to the extracted organic layer to remove water. The remaining solution was concentrated under reduced pressure to obtain 240 g of an ascorbic acid derivative in which the hydroxyl group at the C-6 position was protected by triphenylmethyl chloride.

(e) Synthesis of Ascorbic Acid Derivative in which Succinic Acid is Introduced at the C-5 Position 240 g of the obtained compound was dissolved in 2 L of dichloromethane and dimethylaminopyridine (1.1 eq.) and succinic acid (1.2 eq.) were added. Stirring was performed at 25° C. for 16 hours. Dichloromethane was removed from the solution under reduced pressure. The resultant solution was dissolved in 2 L of ethyl acetate and 2 L of a 5% sodium hydrogen sulphate solution was added. The organic layer was extracted using a separatory funnel. 500 g of anhydrous sodium sulfate was added to the extracted organic layer to remove water. After filtration, the remaining solution was concentrated under reduced pressure. 270 g of a pale yellow, semi-solid compound was obtained from the concentrated solution by silica gel column chromatography (total yield: 27.1%). NMR analysis results for the obtained compound, 3-O-benzyl-2-O-tetramethylphosphorodiamidic-6-O-triphenylmethyl-5-O-succinyl-ascorbic acid are as follows.

$^1$H NMR (CDCl$_3$): 2.63 (tt, 4H, C$\underline{H}_2$C$\underline{H}_2$COOH), 2.7 (m, 12H, P(O)(N(C$\underline{H}_3$)$_2$)$_2$), 3.33 (tt, 2H, C-6-$\underline{H}_2$), 4.98 (s, 1H, C-5-$\underline{H}$), 5.43 (t, H, C-4-$\underline{H}_2$), 5.53 (dd, 2H, O—C$\underline{H}_2$-Ph), 7.33 (m, 20H, Ar—$\underline{H}$)

Example 2

Synthesis of 3-O-benzyl-2-O-tetramethylphosphorodiamidic-5-O-tert-butyloxycarbonyl-6-O-succinyl-ascorbic acid 3-O-benzyl-2-O-tetramethylphosphorodiamidic-5-O-tert-butyloxycarbonyl-6-O-succinyl-ascorbic acid was prepared by the following scheme.

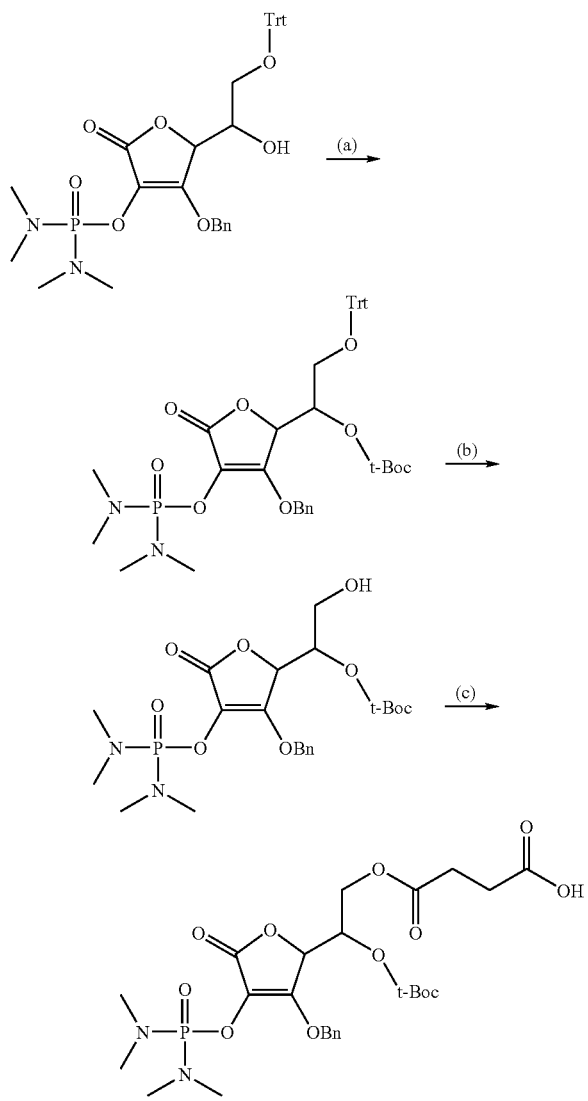

(a) Protection of Hydroxyl Group at the C-5 Position

3-O-benzyl-2-O-tetramethylphosphorodiamidic-6-O-triphenylmethyl-ascorbic acid (100 g, 0.1556 mol) and triethylamine (18 g) were dissolved in 1 L of dichloromethane. Di-tert-butyl dicarbamate (37 g) was added to the solution and stirring was performed at 25° C. for 12 hours. Dichloromethane was removed from the solution under reduced pressure. The resultant solution was dissolved in 1 L of ethyl acetate and 1 L of a 5% sodium hydrogen sulphate solution was added. The organic layer was extracted using a separatory funnel. This procedure was repeated 3 times to remove water-soluble impurities. 300 g of anhydrous sodium sulfate was added to the extracted organic layer to remove water. The remaining solution was concentrated under reduced pressure to obtain 104 g of 3-O-benzyl-2-O-tetramethylphosphorodiamidic-5-O-tert-butyloxycarbonyl-6-O-triphenylmethyl-ascorbic acid in which the hydroxyl group at the C-5 position was protected by a tert-butyloxycarbonyl group.

(b) Deprotection of the C-6 Position 104 g of the obtained compound was dissolved in 1 L of methyl alcohol and the cation exchange resin Dowex50w-8x was added. Stirring was performed at 60° C. for 24 hours. After filtration, methyl alcohol was removed under reduced pressure. The resultant solution was dissolved in 1 L of ethyl acetate and 1 L of a 5% sodium bicarbonate solution was added. The organic layer was extracted using a separatory funnel. 300 g of anhydrous sodium sulfate was added to the extract to remove water. After filtration, the remaining solution was concentrated under reduced pressure to obtain 63 g of an ascorbic acid derivative in which the C-6 position was deprotected and that had a hydroxyl group.

(c) Synthesis of Ascorbic Acid Derivative in which Succinic Acid is Bound at the C-6 Position 63 g of the obtained compound was dissolved in 1 L of dichloromethane and dimethylaminopyridine (1.1 eq.) and succinic acid (1.2 eq.) were added. Stirring was performed at 25° C. for 16 hours. Dichloromethane was removed from the solution under reduced pressure. The resultant solution was dissolved in 1 L of ethyl acetate and 1 L of a 5% sodium hydrogen sulphate solution was added. The organic layer was extracted using a separatory funnel. 300 g of anhydrous sodium sulfate was added to the extract to remove water. After filtration, the remaining solution was concentrated under reduced pressure. 68 g of a pale yellow, semi-solid compound was obtained from the concentrated solution by silica gel column chromatography (total yield: 25%). NMR analysis results for the obtained compound, 3-O-benzyl-2-O-tetramethylphosphorodiamidic-5-O-tert-butyloxycarbonyl-6-O-succinyl-ascorbic acid, are as follows.

$^1$H NMR (CDCl$_3$): 1.42 (s, 9H, OC(C$\underline{H}_3$)$_3$), 2.63 (tt, 4H, C$\underline{H}_2$CH$_2$COOH), 2.7 (m, 12H, P(O)(N(C$\underline{H}_3$)$_2$)$_2$), 3.33 (tt, 2H, C-6-$\underline{H}_2$), 4.98 (s, 1H, C-5-$\underline{H}$), 5.43 (t, H, C-4-$\underline{H}_2$), 5.53 (dd, 2H, O—C$\underline{H}_2$-Ph), 7.33 (m, 5H, Ar—$\underline{H}$)

Example 3

Synthesis of 3-O-benzyl-2-O-tetramethylphosphorodiamidic-5-O-palmitoyl-6-O-succinyl-ascorbic acid 3-O-benzyl-2-O-tetramethylphosphorodiamidic-5-O-palmitoyl-6-O-succinyl-ascorbic acid was prepared by the following scheme.

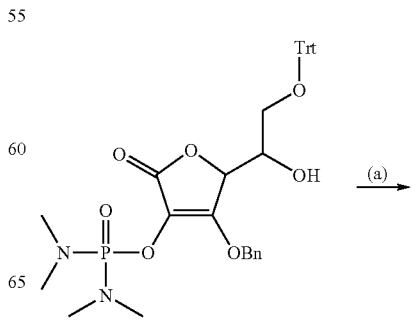

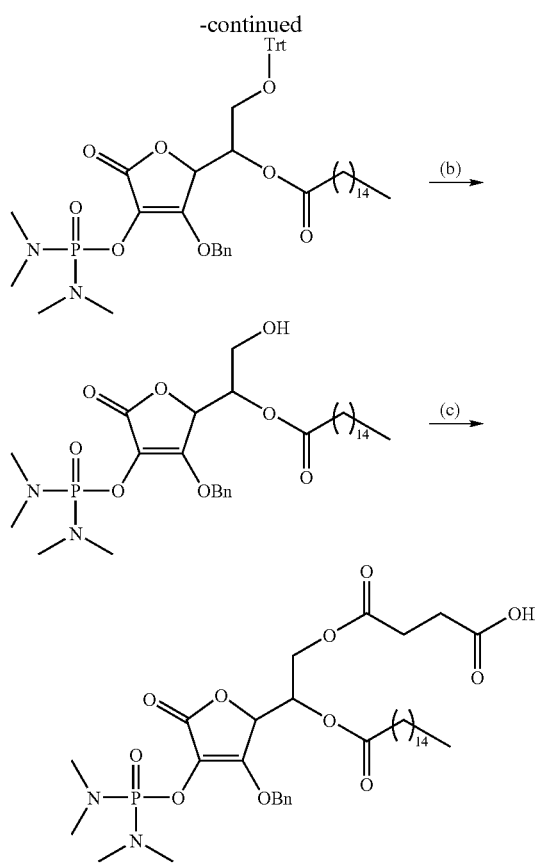

(a) Introduction of Palmitoyl Group at the C-5 Position 10 g of 3-O-benzyl-2-O-tetramethylphosphorodiamidic-6-O-triphenylmethyl-ascorbic acid and 2 g of triethylamine were dissolved in 100 mL of dichloromethane and 5 g of palmitoyl chloride was added. Then, stirring was performed at 25° C. for 16 hours. Dichloromethane was removed from the solution under reduced pressure. The resultant solution was dissolved in 100 mL of ethyl acetate and 100 mL of a 5% sodium hydrogen sulphate solution was added. The organic layer was extracted using a separatory funnel. 30 g of anhydrous sodium sulfate was added to the extract to remove water. After filtration, the remaining solution was concentrated under reduced pressure to obtain 10 g of an ascorbic acid derivative in which a palmitoyl group is introduced at the C-5 position.

(b) Deprotection of the C-6 Position 10 g of the obtained compound was dissolved in 100 mL of methyl alcohol and the cation exchange resin Dowex50w-8x was added. Then, stirring was performed at 60° C. for 24 hours. After filtration, methyl alcohol was removed under reduced pressure. The resultant solution was dissolved in 100 mL of ethyl acetate and 100 mL of a 5% sodium bicarbonate solution was added. The organic layer was extracted using a separatory funnel. 30 g of anhydrous sodium sulfate was added to the extract to remove water. After filtration, the remaining solution was concentrated under reduced pressure to obtain 5 g of an ascorbic acid derivative in which the C-6 position was deprotected and that had a hydroxyl group.

(c) Introduction of Succinic Acid at the C-6 Position 5 g of the obtained compound was dissolved in 50 mL of dichloromethane and dimethylaminopyridine (1.1 eq.) and succinic acid (1.2 eq.) were added. Then, stirring was performed at 25° C. for 16 hours. Dichloromethane was removed from the solution under reduced pressure. The resultant solution was dissolved in 50 mL of ethyl acetate and 50 mL of a 5% sodium hydrogen sulphate solution was added. The organic layer was extracted using a separatory funnel. 10 g of anhydrous sodium sulfate was added to the extract to remove water. After filtration, the remaining solution was concentrated under reduced pressure. 5 g of a pale yellow, semi-solid compound was obtained from the concentrated solution by silica gel column chromatography (total yield: 13.3%). NMR analysis results for the obtained compound, 3-O-benzyl-2-O-tetramethylphosphorodiamidic-5-O-palmitoyl-6-O-succinyl-ascorbic acid, are as follows.

$^1$H NMR (CDCl$_3$): 0.88 (t, 3H, C(O)CH$_2$(CH$_2$)$_{13}$C$\underline{H}_3$), 1.28 (m, 26H, C(O)CH$_2$(C$\underline{H}_2$)$_{13}$CH$_3$), 2.53 (t, 2H, C(O)C$\underline{H}_2$(CH$_2$)$_{13}$CH$_3$), 2.59 (tt, 4H, C$\underline{H}_2$C$\underline{H}_2$COOH), 2.7 (m, 12H, P(O)(N(C$\underline{H}_3$)$_2$)$_2$), 3.33 (tt, 2H, C-6-$\underline{H}_2$), 4.98 (s, 1H, C-5-$\underline{H}$), 5.43 (t, H, C-4-$\underline{H}_2$), 5.53 (dd, 2H, O—C$\underline{H}_2$-Ph), 7.33 (m, 5H, Ar—$\underline{H}$)

Example 4

Synthesis of 3-O-benzyl-2-O-tetramethylphosohorodiamidic-6-O-palmitoyl-5-O-succinyl-ascorbic acid 3-O-benzyl-2-O-tetramethylphosphorodiamidic-6-O-palmitoyl-5-O-succinyl-ascorbic acid was prepared by the following scheme.

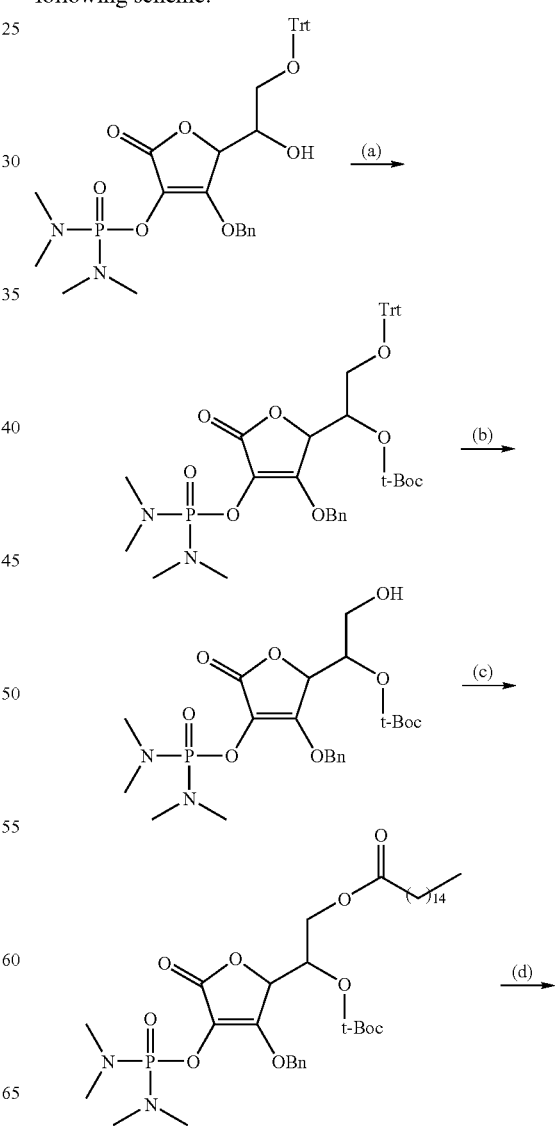

-continued

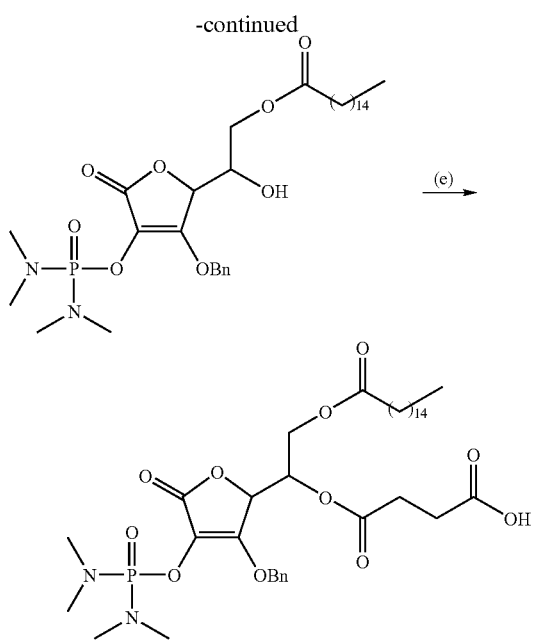

(a) Protection of Hydroxyl Group at the C-5 Position

3-O-benzyl-2-O-tetra methylphosphorodiamidic-6-O-triphenylmethyl-ascorbic acid (10 g, 15.56 mmol) and triethylamine (1.8 g) were dissolved in 100 mL of dichloromethane and di-tert-butyl dicarbamate (3.7 g) was added. Then, stirring was performed at 25° C. for 12 hours. Dichloromethane was removed from the solution under reduced pressure. The resultant solution was dissolved in 100 mL of ethyl acetate and 100 mL of a 5% sodium hydrogen sulphate solution was added. The organic layer was extracted using a separatory funnel. This procedure was repeated 3 times to remove water-soluble impurities. 30 g of anhydrous sodium sulfate was added to the organic layer to remove water. After filtration, the remaining solution was concentrated under reduced pressure to obtain 10 g of 3-O-benzyl-2-O-tetramethylphosphorodiamidic-5-O-tert-butyloxycarbonyl-6-O-triphenylmethyl-ascorbic acid in which the hydroxyl group at the C-5 position is protected by a tert-butyloxycarbonyl group.

(b) Deprotection of the C-6 Position 10 g of the obtained compound was dissolved in 100 mL of methyl alcohol and the cation exchange resin Dowex50w-8x was added. Then, stirring was performed at 60° C. for 24 hours. After filtration, methyl alcohol was removed under reduced pressure. The resultant solution was dissolved in 100 mL of ethyl acetate and 100 mL of a 5% sodium bicarbonate solution was added. The organic layer was extracted using a separatory funnel. 30 g of anhydrous sodium sulfate was added to the extract to remove water. After filtration, the remaining solution was concentrated under reduced pressure to obtain 6.3 g of an ascorbic acid derivative in which the C-6 position was deprotected and that had a hydroxyl group.

(c) Introduction of Palmitoyl Group at the C-6 Position 6.3 g of the obtained compound and 2 g of triethylamine were dissolved in 100 mL of dichloromethane and 5 g of palmitoyl chloride was added. Then, stirring was performed at 25° C. for 16 hours. Dichloromethane was removed from the solution under reduced pressure. The resultant solution was dissolved in 100 mL of ethyl acetate and 100 mL of a 5% sodium hydrogen sulphate solution was added. The organic layer was extracted using a separatory funnel. 30 g of anhydrous sodium sulfate was added to the extract to remove water. After filtration, the remaining solution was concentrated under reduced pressure to obtain 10 g of an ascorbic acid derivative in which a palmitoyl was introduced at the C-6 position.

(d) Deprotection of the C-5 Position 10 g of the obtained compound was dissolved in 100 mL of methyl alcohol and the cation exchange resin Dowex50w-8x was added. Then, stirring was performed at 60° C. for 48 hours. After filtration, methyl alcohol was removed under reduced pressure. 100 mL of ethyl acetate was dissolved in the resultant solution and 100 mL of a 5% sodium bicarbonate solution was added. The organic layer was extracted using a separatory funnel. 30 g of anhydrous sodium sulfate was added to the extract to remove water. After filtration, the remaining solution was concentrated under reduced pressure to obtain 5 g of an ascorbic acid derivative in which the C-5 position is deprotected and has a hydroxyl group.

(e) Introduction of Succinic Acid at the C-5 Position 5 g of the obtained compound was dissolved in 50 mL of dichloromethane and dimethylaminopyridine (1.1 eq.) and succinic acid (1.2 eq.) were added. Then, stirring was performed at 25° C. for 16 hours. Dichloromethane was removed from the solution under reduced pressure. The resultant solution was dissolved in 50 mL of ethyl acetate and 50 mL of a 5% sodium hydrogen sulphate solution was added. The organic layer was extracted using a separatory funnel. 10 g of anhydrous sodium sulfate was added to the extract to remove water. After filtration, the remaining solution was concentrated under reduced pressure. 4.8 g of a pale yellow, semi-solid compound was obtained from the concentrated solution by silica gel column chromatography (total yield: 12%). NMR analysis results for the obtained compound, 3-O-benzyl-2-O-tetramethylphosphorodiamidic-6-O-palmitoyl-5-O-succinyl-ascorbic acid, are as follows.

$^1$H NMR (CDCl$_3$): 0.88 (t, 3H, C(O)CH$_2$(CH$_2$)$_{13}$C$\underline{H}_3$), 1.28 (m, 26H, C(O)CH$_2$(C$\underline{H}_2$)$_{13}$CH$_3$), 2.53 (t, 2H, C(O)C$\underline{H}_2$(CH$_2$)$_{13}$CH$_3$), 2.59 (tt, 4H, C$\underline{H}_2$C$\underline{H}_2$COOH), 2.7 (m, 12H, P(O)(N(C$\underline{H}_3$)$_2$)$_2$), 3.33 (ft, 2H, C-6-$\underline{H}_2$), 4.98 (s, 1H, C-5-$\underline{H}$), 5.43 (t, H, C-4-$\underline{H}_2$), 5.53 (dd, 2H, O—C$\underline{H}_2$-Ph), 7.33 (m, 5H, Ar—$\underline{H}$)

Example 5

Synthesis of Peptides

Peptide synthesis was performed by solid phase synthesis using Fmoc (9-fluorenylmethoxycarbonyl) as the protecting group of the N-α-amino acid. The peptide chain was elongated by the HOBt-DCC(N-hydroxybenzotriazole-dicyclohexylcarodiimide) method (Wang C. Chan, Perter D. White, "Fmoc solid phase peptide synthesis" Oxford). Glycine-histidine-lysine (GHK), glycine-lysine-histidine (GKH), glycine-proline-hydroxyproline (GPO), lysine-threonine-threonine-lysine-serine (KTTKS), and glutamic acid-glutamic acid-methionine-glutamine-arginine-arginine (EEMQRR) peptides were synthesized.

Example 6

Synthesis of Stabilized Vitamin C Derivative with a Peptide Molecule 6-1: Synthesis of the Compound Represented by Chemical Formula Ia 50 mL of a 20% piperidine/N-methylpyrrolidone solution was added to the peptide prepared in Example 5 (1 mmol), in which up to the amino acid at the N-terminus is coupled, to remove the Fmoc group. After washing with N-methylpyrrolidone and dichloromethane, the vitamin C derivative prepared in Example 1 was coupled. After coupling was completed, the peptide was washed several times with N-methylpyrrolidone and dichloromethane and dried with nitrogen gas. Then, 50 mL of trifluoroacetic acid was added and reaction was performed at 25° C. for 3 hours to remove the peptide protecting group and the triphenylmethyl group that protects protects the alcohol group at the C-6 position of vitamin C. The stabilized vitamin C derivative with a peptide molecule was separated from the resin and the peptide was precipitated with diethyl ether.

In order to remove the benzyl group that protects the alcohol group at the C-3 position of vitamin C, 0.1 g of 10% Pd/C was added to 50 mL of methanol and stirring was performed at 25° C. for about 1 hour under a hydrogen atmosphere. Pd/C was removed using celite and the remaining solution was concentrated under reduced pressure. The obtained vitamin C derivative was purified by reverse phase high-performance liquid column chromatography (Zobax, C8 300 Å, 21.1 mm×25 cm) using acetonitrile containing 0.1% trifluoroacetic acid and celite to obtain 0.5 g of the stabilized vitamin C derivative with a peptide molecule represented by Chemical Formula 1a (compounds Ia-1 to Ia-5 in Table 1 below). 6-2: Synthesis of the compound represented by Chemical Formula Ib 50 mL of 20% piperidine/N-methylpyrrolidone solution was added to the peptide prepared in Example 5 (1 mmol), in which up to the amino acid at the N-terminus was coupled, to remove the Fmoc group. After washing with N-methylpyrrolidone and dichloromethane, the vitamin C derivative prepared in Example 2 was coupled. After coupling was completed, the peptide was washed several times with N-methylpyrrolidone and dichloromethane and dried with nitrogen gas. Then, 50 mL of trifluoroacetic acid was added and reaction was performed at 25° C. for 3 hours to remove the peptide protecting group and the tert-butyloxycarbonyl group that protects the alcohol group at the C-5 position of vitamin C. The stabilized vitamin C derivative with a peptide molecule was separated from the resin and the peptide was precipitated with diethyl ether.

In order to remove the benzyl group that protects the alcohol group at the C-3 position of vitamin C, 0.1 g of 10% Pd/C was added to 50 mL of methanol and stirring was performed at 25° C. for about 1 hour under a hydrogen atmosphere. Pd/C was removed using celite and the remaining solution was concentrated under reduced pressure. The obtained vitamin C derivative was purified by reverse phase high-performance liquid column chromatography (Zobax, C8 300 Å, 21.1 mm×25 cm) using acetonitrile containing 0.1% trifluoroacetic acid and celite to obtain 0.5 g of the stabilized vitamin C derivative with a peptide molecule represented by Chemical Formula 1b (compounds Ib-1 to Ib-5 in Table 1).

6-3: Synthesis of the Compound Represented by Chemical Formula Ic 0.5 g of the compound represented by Chemical Formula Ia, which was prepared in Example 6-1, was dissolved in 50 mL of third purified water and 0.5 g of the cation exchange resin Dowex 50w-8x was added. Then, stirring was performed at 25° C. for 24 hours. After filtration, 500 mL of ethanol was added to the remaining solution to form solids, which were filtered and dried under vacuum to obtain 0.4 g of the stabilized vitamin C derivative with a peptide molecule represented by Chemical Formula Ic (compounds Ic-1 to Ic-5 in Table 1).

6-4: Synthesis of the Compound Represented by Chemical Formula Id 0.5 g of the compound represented by Chemical Formula Ib, which was prepared in Example 6-2, was dissolved in 50 mL of third purified water and 0.5 g of the cation exchange resin Dowex 50w-8x was added. Then, stirring was performed at 25° C. for 24 hours. After filtration, 500 mL of ethanol was added to the remaining solution to form solids, which were filtered and dried under vacuum to obtain 0.4 g of the stabilized vitamin C derivative with a peptide molecule represented by Chemical Formula 1d (compounds Id-1 to Id-5 in Table 1).

6-5: Synthesis of the Compound Represented by Chemical Formula 2a 50 mL of 20% piperidine/N-methylpyrrolidone solution was added to the peptide prepared in Example 5 (1 mmol), in which up to the amino acid at the N-terminus was coupled, to remove the Fmoc group. After washing with N-methylpyrrolidone and dichloromethane, the vitamin C derivative prepared in Example 3 was coupled. After coupling was completed, the peptide was washed several times with N-methylpyrrolidone and dichloromethane and dried with nitrogen gas. Then, 50 mL of trifluoroacetic acid was added and reaction was performed at 25° C. for 3 hours to remove the peptide protecting group. The stabilized vitamin C derivative with a peptide molecule was separated from the resin and the peptide was precipitated with diethyl ether.

In order to remove the benzyl group that protects the alcohol group at the C-3 position of vitamin C, 0.1 g of 10% Pd/C was added to 50 mL of methanol and stirring was performed at 25° C. for about 1 hour under a hydrogen atmosphere. Pd/C was removed using celite and the remaining solution was concentrated under reduced pressure. The obtained vitamin C derivative was purified by reverse phase high-performance liquid column chromatography (Zobax, C8 300 Å, 21.1 mm×25 cm) using acetonitrile containing 0.1% trifluoroacetic acid and celite to obtain 0.6 g of the stabilized vitamin C derivative with a peptide molecule represented by Chemical Formula 2a (compounds IIa-1 to IIa-5 in Table 1).

6-6: Synthesis of the Compound Represented by Chemical Formula 2b 50 mL of 20% piperidine/N-methylpyrrolidone solution was added to the peptide prepared in Example 5 (1 mmol), in which up to the amino acid at the N-terminus was coupled, to remove the Fmoc group. After washing with N-methylpyrrolidone and dichloromethane, the vitamin C derivative prepared in Example 4 was coupled. After coupling was completed, the peptide was washed several times with N-methylpyrrolidone and dichloromethane and dried with nitrogen gas. Then, 50 mL of trifluoroacetic acid was added and reaction was performed at 25° C. for 3 hours to remove the peptide protecting group. The stabilized vitamin C derivative with a peptide molecule was separated from the resin and the peptide was precipitated with diethyl ether.

In order to remove the benzyl group that protects the alcohol group at the C-3 position of vitamin C, 0.1 g of 10% Pd/C was added to 50 mL of methanol and stirring was performed at 25° C. for about 1 hour under a hydrogen atmosphere. Pd/C was removed using celite and the remaining solution was concentrated under reduced pressure. The obtained vitamin C derivative was purified by reverse phase high-performance liquid column chromatography (Zobax, C8 300 Å, 21.1 mm×25 cm) using acetonitrile containing 0.1% trifluoroacetic acid and celite to obtain 0.6 g of the stabilized vitamin C derivative with a peptide molecule represented by Chemical Formula 2b (compounds IIb-1 to IIb-5 in Table 1).

6-7: Synthesis of the Compound Represented by Chemical Formula 2c 0.5 g of the compound represented by Chemical Formula 2a, which was prepared in Example 6-5, was dissolved in 50 mL of third purified water and 0.5 g of the cation exchange resin Dowex 50w-8x was added. Then, stirring was performed at 25° C. for 24 hours. After filtration, 500 mL of ethanol was added to the remaining solution to form solids, which were filtered and dried under vacuum to obtain 0.5 g of the stabilized vitamin C derivative with a peptide molecule represented by Chemical Formula 2c (compounds IIc-1 to IIc-5 in Table 1).

6-8: Synthesis of the Compound Represented by Chemical Formula 2d 0.5 g of the compound represented by Chemical Formula 1b, which was prepared in Example 6-2, was dissolved in 50 mL of third purified water and 0.5 g of the cation exchange resin Dowex 50w-8x was added. Then, stirring was performed at 25° C. for 24 hours. After filtration, 500 mL of ethanol was added to the remaining solution to form solids, which were filtered and dried under vacuum to obtain 0.5 g of the stabilized vitamin C derivative with a peptide molecule represented by Chemical Formula 2d (compounds IId-1 to IId-5 in Table 1).

In Table 1, the compounds Ia, Ib, Ic, Id, IIa, IIb, IIc, and IId are the compounds represented by Chemical Formulae 1a, 1b, 1c, 1d, 2a, 2b, 2c, and 2d, respectively.

[Compound Ia-1] $^1$H NMR ($D_2O$): 0.95 (m, peptide-H), 1.22 (m, peptide-H), 1.55 (m, peptide-H), 2.52 (m, 4H, C$\underline{H}_2$C$\underline{H}_2$CONH), 2.70 (m, 12H, P(O)(N(C$\underline{H}_3)_2)_2$), 3.33 (tt, 2H, C-6-$\underline{H}_2$), 4.21 (m, peptide-H), 4.98 (s, 1 H, C-5-$\underline{H}$), 5.43 (t, H, C-4-$\underline{H}_2$))

[Compound Ia-2] $^1$H NMR ($D_2O$): 0.93 (m, peptide-H), 1.22 (m, peptide-H), 1.66 (m, peptide-H), 2.52 (m, 4H, C$\underline{H}_2$C$\underline{H}_2$CONH), 2.70 (m, 12H, P(O)(N(C$\underline{H}_3)_2)_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Ia-3] $^1$H NMR ($D_2O$): 0.93 (m, peptide-H), 1.22 (m, peptide-H), 1.66 (m, peptide-H), 2.52 (m, 4H, C$\underline{H}_2$C$\underline{H}_2$CONH), 2.70 (m, 12H, P(O)(N(C$\underline{H}_3)_2)_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Ia-4] $^1$H NMR ($D_2O$): 2.01 (m, peptide-H), 2.52 (m, 4H, C$\underline{H}_2$C$\underline{H}_2$CONH), 2.70 (m, 12H, P(O)(N(C$\underline{H}_3)_2)_2$), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-$\underline{H}_2$)

[Compound Ia-5] $^1$H NMR ($D_2O$): 0.91 (m, peptide-H), 1.55 (m, peptide-H), 2.13 (m, peptide-H), 2.42 (m, peptide-H), 2.52 (m, 4H, C$\underline{H}_2$C$\underline{H}_2$CONH), 2.61 (m, peptide-H), 2.70 (m, 12H, P(O)(N(C$\underline{H}_3)_2)_2$), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

TABLE 1

| Compd. NO. | 5' carbon of Vitamin C | 6' carbon of Vitamin C | W | MS molecular weight Theoretical | MS molecular weight Measured |
|---|---|---|---|---|---|
| Ia-1 | -X-KTTKS | —OH | —OP(O)N($CH_3)_2$ | 956.02 | 957.1 |
| Ia-2 | -X-GHK | —OH | —OP(O)N($CH_3)_2$ | 732.72 | 733.4 |
| Ia-3 | -X-GKH | —OH | —OP(O)N($CH_3)_2$ | 732.72 | 733.4 |
| Ia-4 | -X-GPO | —OH | —OP(O)N($CH_3)_2$ | 677.62 | 678.1 |
| Ia-5 | -X-EEMQRR | —OH | —OP(O)N($CH_3)_2$ | 1270.22 | 1271.1 |
| Ib-1 | —OH | -X-KTTKS | —OP(O)N($CH_3)_2$ | 956.02 | 957.1 |
| Ib-2 | —OH | -X-GHK | —OP(O)N($CH_3)_2$ | 732.72 | 733.4 |
| Ib-3 | —OH | -X-GKH | —OP(O)N($CH_3)_2$ | 732.72 | 733.4 |
| Ib-4 | —OH | -X-GPO | —OP(O)N($CH_3)_2$ | 677.62 | 678.1 |
| Ib-5 | —OH | -X-EEMQRR | —OP(O)N($CH_3)_2$ | 1270.22 | 1271.1 |
| Ic-1 | -X-KTTKS | —OH | —OP(O)(OH)$_2$ | 901.88 | 902.2 |
| Ic-2 | -X-GHK | —OH | —OP(O)(OH)$_2$ | 678.58 | 679.3 |
| Ic-3 | -X-GKH | —OH | —OP(O)(OH)$_2$ | 678.58 | 679.3 |
| Ic-4 | -X-GPO | —OH | —OP(O)(OH)$_2$ | 623.48 | 624.2 |
| Ic-5 | -X-EEMQRR | —OH | —OP(O)(OH)$_2$ | 1186.08 | 1187.1 |
| Id-1 | —OH | -X-KTTKS | —OP(O)(OH)$_2$ | 901.88 | 902.2 |
| Id-2 | —OH | -X-GHK | —OP(O)(OH)$_2$ | 678.58 | 679.3 |
| Id-3 | —OH | -X-GKH | —OP(O)(OH)$_2$ | 678.58 | 679.3 |
| Id-4 | —OH | -X-GPO | —OP(O)(OH)$_2$ | 623.48 | 624.2 |
| Id-4 | —OH | -X-EEMQRR | —OP(O)(OH)$_2$ | 1186.08 | 1187.1 |
| IIa-1 | -X-KTTKS | —OC(O)($CH_2)_{14}CH_3$ | —OP(O)N($CH_3)_2$ | 1284.56 | 1285.3 |
| IIa-2 | -X-GHK | —OC(O)($CH_2)_{14}CH_3$ | —OP(O)N($CH_3)_2$ | 1061.26 | 1062.1 |
| IIa-3 | -X-GKH | —OC(O)($CH_2)_{14}CH_3$ | —OP(O)N($CH_3)_2$ | 1061.26 | 1062.1 |
| IIa-4 | -X-GPO | —OC(O)($CH_2)_{14}CH_3$ | —OP(O)N($CH_3)_2$ | 1006.16 | 1007.1 |
| IIa-5 | -X-EEMQRR | —OC(O)($CH_2)_{14}CH_3$ | —OP(O)N($CH_3)_2$ | 1568.76 | 1569.5 |
| IIb-1 | —OC(O)($CH_2)_{14}CH_3$ | -X-KTTKS | —OP(O)N($CH_3)_2$ | 1284.56 | 1286.3 |
| IIb-2 | —OC(O)($CH_2)_{14}CH_3$ | -X-GHK | —OP(O)N($CH_3)_2$ | 1061.26 | 1062.1 |
| IIb-3 | —OC(O)($CH_2)_{14}CH_3$ | -X-GKH | —OP(O)N($CH_3)_2$ | 1061.26 | 1062.1 |
| IIb-4 | —OC(O)($CH_2)_{14}CH_3$ | -X-GPO | —OP(O)N($CH_3)_2$ | 1006.16 | 1007.1 |
| IIb-5 | —OC(O)($CH_2)_{14}CH_3$ | -X-EEMQRR | —OP(O)N($CH_3)_2$ | 1568.76 | 1569.5 |
| IIc-1 | -X-KTTKS | —OC(O)($CH_2)_{14}CH_3$ | —OP(O)(OH)$_2$ | 1230.42 | 1231.3 |
| IIc-2 | -X-GHK | —OC(O)($CH_2)_{14}CH_3$ | —OP(O)(OH)$_2$ | 1007.12 | 1008.1 |
| IIc-3 | -X-GKH | —OC(O)($CH_2)_{14}CH_3$ | —OP(O)(OH)$_2$ | 1007.12 | 1008.1 |
| IIc-4 | -X-GPO | —OC(O)($CH_2)_{14}CH_3$ | —OP(O)(OH)$_2$ | 952.02 | 953.1 |
| IIc-5 | -X-EEMQRR | —OC(O)($CH_2)_{14}CH_3$ | —OP(O)(OH)$_2$ | 1514.62 | 1515.4 |
| IId-1 | —OC(O)($CH_2)_{14}CH_3$ | -X-KTTKS | —OP(O)(OH)$_2$ | 1230.42 | 1231.3 |
| IId-2 | —OC(O)($CH_2)_{14}CH_3$ | -X-GHK | —OP(O)(OH)$_2$ | 1007.12 | 1008.1 |
| IId-3 | —OC(O)($CH_2)_{14}CH_3$ | -X-GKH | —OP(O)(OH)$_2$ | 1007.12 | 1008.1 |
| IId-4 | —OC(O)($CH_2)_{14}CH_3$ | -X-GPO | —OP(O)(OH)$_2$ | 952.02 | 953.1 |
| IId-5 | —OC(O)($CH_2)_{14}CH_3$ | -X-EEMQRR | —OP(O)(OH)$_2$ | 1514.62 | 1515.4 |

[Compound Ib-1] $^1$H NMR (D$_2$O): 0.95 (m, peptide-H), 1.22 (m, peptide-H), 1.55 (m, peptide-H), 2.52 (m, 4H, C$\underline{H}_2$C$\underline{H}_2$CONH), 2.70 (m, 12H, P(O)(N(C$\underline{H}_3$)$_2$)$_2$), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound Ib-2] $^1$H NMR (D$_2$O): 0.93 (m, peptide-H), 1.22 (m, peptide-H), 1.66 (m, peptide-H), 2.52 (m, 4H, C$\underline{H}_2$C$\underline{H}_2$CONH), 2.70 (m, 12H, P(O)(N(C$\underline{H}_3$)$_2$)$_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Ib-3] $^1$H NMR (D$_2$O): 0.93 (m, peptide-H), 1.22 (m, peptide-H), 1.66 (m, peptide-H), 2.52 (m, 4H, C$\underline{H}_2$C$\underline{H}_2$CONH), 2.70 (m, 12H, P(O)(N(C$\underline{H}_3$)$_2$)$_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Ib-4] $^1$H NMR (D$_2$O): 2.01 (m, peptide-H), 2.52 (m, 4H, C$\underline{H}_2$C$\underline{H}_2$CONH), 2.70 (m, 12H, P(O)(N(C$\underline{H}_3$)$_2$)$_2$), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-H), 5.43 (t, H, C-4-$\underline{H}_2$)

[Compound Ib-5] $^1$H NMR (D$_2$O): 0.91 (m, peptide-H), 1.55 (m, peptide-H), 2.13 (m, peptide-H), 2.42 (m, peptide-H), 2.52 (m, 4H, C$\underline{H}_2$C$\underline{H}_2$CONH), 2.61 (m, peptide-H), 2.70 (m, 12H, P(O)(N(C$\underline{H}_3$)$_2$)$_2$), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$) compound Ic-1] $^1$H NMR (D$_2$O): 0.95 (m, peptide-H), 1.22 (m, peptide-H), 1.55 (m, peptide-H), 2.52 (m, 4H, C$\underline{H}_2$C$\underline{H}_2$CONH), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound Ic-2] $^1$H NMR (D$_2$O): 0.93 (m, peptide-H), 1.22 (m, peptide-H), 1.66 (m, peptide-H), 2.52 (m, 4H, C$\underline{H}_2$C$\underline{H}_2$CONH), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Ic-3] $^1$H NMR (D$_2$O): 0.93 (m, peptide-H), 1.22 (m, peptide-H), 1.66 (m, peptide-H), 2.52 (m, 4H, C$\underline{H}_2$C$\underline{H}_2$CONH), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Ic-4] $^1$H NMR (D$_2$O): 2.01 (m, peptide-H), 2.52 (m, 4H, C$\underline{H}_2$C$\underline{H}_2$CONH), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-$\underline{H}_2$)

[Compound Ic-5] $^1$H NMR (D$_2$O): 0.91 (m, peptide-H), 1.55 (m, peptide-H), 2.13 (m, peptide-H), 2.42 (m, peptide-H), 2.52 (m, 4H, C$\underline{H}_2$C$\underline{H}_2$CONH), 2.61 (m, peptide-H), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

[Compound Id-1] $^1$H NMR (D$_2$O): 0.95 (m, peptide-H), 1.22 (m, peptide-H), 1.55 (m, peptide-H), 2.52 (m, 4H, C$\underline{H}_2$C$\underline{H}_2$CONH), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound Id-2] $^1$H NMR (D$_2$O): 0.93 (m, peptide-H), 1.22 (m, peptide-H), 1.66 (m, peptide-H), 2.52 (m, 4H, C$\underline{H}_2$C$\underline{H}_2$CONH), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Id-3] $^1$H NMR (D$_2$O): 0.93 (m, peptide-H), 1.22 (m, peptide-H), 1.66 (m, peptide-H), 2.52 (m, 4H, C$\underline{H}_2$C$\underline{H}_2$CONH), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound Id-4] $^1$H NMR (D$_2$O): 2.01 (m, peptide-H), 2.52 (m, 4H, C$\underline{H}_2$C$\underline{H}_2$CONH), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-$\underline{H}_2$)

[Compound Id-5] $^1$H NMR (D$_2$O): 0.91 (m, peptide-H), 1.55 (m, peptide-H), 2.13 (m, peptide-H), 2.42 (m, peptide-H), 2.52 (m, 4H, C$\underline{H}_2$C$\underline{H}_2$CONH), 2.61 (m, peptide-H), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

[Compound IIa-1] $^1$H NMR (D$_2$O): 0.88 (t, 3H, C(O)CH$_2$(CH$_2$)$_{13}$C$\underline{H}_3$), 0.95 (m, peptide-H), 1.22 (m, peptide-H), 1.28 (m, 26H, C(O)CH$_2$(C$\underline{H}_2$)$_{13}$CH$_3$), 1.55 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$^3$), 2.70 (m, 12H, P(O)(N(CH3)2)2), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound IIa-2] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IIa-3] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IIa-4] $^1$H NMR (D$_2$O): 0.88 (t, 3H, C(O)CH$_2$(CH$_2$)$_{13}$C$\underline{H}_3$), 1.28 (m, 26H, C(O)CH$_2$(C$\underline{H}_2$)$_{13}$CH$_3$), 2.01 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-$\underline{H}_2$)

[Compound IIa-5] $^1$H NMR (D$_2$O): 0.88 (t, 3H, C(O)CH$_2$(CH$_2$)$_{13}$C$\underline{H}_3$), 0.91 (m, peptide-H), 1.28 (m, 26H, C(O)CH$_2$(C$\underline{H}_2$)$_{13}$CH$_3$), 1.55 (m, peptide-H), 2.13 (m, peptide-H), 2.42 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.61 (m, peptide-H), 2.70 (m, 12H, P(O)(N(C$\underline{H}_3$)$_2$)$_2$), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

[Compound IIb-1] $^1$H NMR (D$_2$O): 0.88 (t, 3H, C(O)CH$_2$(CH$_2$)$_{13}$C$\underline{H}_3$), 0.95 (m, peptide-H), 1.22 (m, peptide-H), 1.28 (m, 26H, C(O)CH$_2$(C$\underline{H}_2$)$_{13}$CH$_3$), 1.55 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound IIb-2] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IIb-3] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IIb-4] $^1$H NMR (D$_2$O): 0.88 (t, 3H, C(O)CH$_2$(CH$_2$)$_{13}$C$\underline{H}_3$), 1.28 (m, 26H, C(O)CH$_2$(C$\underline{H}_2$)$_{13}$CH$_3$), 2.01 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.70 (m, 12H, P(O)(N(C$\underline{H}_3$)$_2$)$_2$), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-H2)

[Compound IIb-5] $^1$H NMR (D$_2$O): 0.88 (t, 3H, C(O)CH$_2$(CH$_2$)$_{13}$C$\underline{H}_3$), 0.91 (m, peptide-H), 1.28 (m, 26H, C(O)CH$_2$(C$\underline{H}_2$)$_{13}$CH$_3$), 1.55 (m, peptide-H), 2.13 (m, peptide-H), 2.42 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.61 (m, peptide-H), 2.70 (m, 12H, P(O)(N(C$\underline{H}_3$)$_2$)$_2$), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

[Compound IIc-1] $^1$H NMR (D$_2$O): 0.88 (t, 3H, C(O)CH$_2$(CH$_2$)$_{13}$C$\underline{H}_3$), 0.95 (m, peptide-H), 1.22 (m, peptide-H), 1.28 (m, 26H, C(O)CH$_2$(C$\underline{H}_2$)$_{13}$CH$_3$), 1.55 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound IIc-2] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IIc-3] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IIc-4] $^1$H NMR (D$_2$O): 0.88 (t, 3H, C(O)CH$_2$(CH$_2$)$_{13}$C$\underline{H}_3$), 1.28 (m, 26H, C(O)CH$_2$(C$\underline{H}_2$)$_{13}$CH$_3$), 2.01 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-$\underline{H}_2$)

[Compound IIc-5] $^1$H NMR (D$_2$O): 0.88 (t, 3H, C(O)CH$_2$(CH$_2$)$_{13}$C$\underline{H}_3$), 0.91 (m, peptide-H), 1.28 (m, 26H, C(O)CH$_2$(C$\underline{H}_2$)$_{13}$CH$_3$), 1.55 (m, peptide-H), 2.13 (m, peptide-H), 2.42 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.61 (m, peptide-H), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

[Compound IId-1] $^1$H NMR (D$_2$O): 0.88 (t, 3H, C(O)CH$_2$(CH$_2$)$_{13}$C$\underline{H}_3$), 0.95 (m, peptide-H), 1.22 (m, peptide-H), 1.28 (m, 26H, C(O)CH$_2$(C$\underline{H}_2$)$_{13}$CH$_3$), 1.55 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.33 (tt, 2H, C-6-$\underline{H}_2$), 4.21 (m, peptide-H), 4.98 (s, 1H, C-5-$\underline{H}$), 5.43 (t, H, C-4-$\underline{H}_2$)

[Compound IId-2] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IId-3] $^1$H NMR (D$_2$O): 0.88 (t, 3H, C(O)CH$_2$(CH$_2$)$_{13}$C$\underline{H}_3$), 0.93 (m, peptide-H), 1.22 (m, peptide-H), 1.28 (m, 26H, C(O)CH$_2$(C$\underline{H}_2$)$_{13}$CH$_3$), 1.66 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.17 (m, peptide-H), 3.33 (tt, 2H, C-6-$\underline{H}_2$), 4.08 (s, 2H, peptide-H), 4.55 (m, peptide-H), 4.98 (s, 1H, C-5-$\underline{H}$), 5.43 (t, H, C-4-$\underline{H}_2$)

[Compound IId-4] $^1$H NMR (D$_2$O): 0.88 (t, 3H, C(O)CH$_2$(CH$_2$)$_{13}$C$\underline{H}_3$), 1.28 (m, 26H, C(O)CH$_2$(C$\underline{H}_2$)$_{13}$CH$_3$), 2.01 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 3.33 (tt, 2H, C-6-$\underline{H}_2$), 3.51 (m, peptide-H), 4.09 (s, 2H, peptide-H), 4.40 (m, peptide-H), 4.98 (s, 1H, C-5-$\underline{H}$), 5.43 (t, H, C-4-$\underline{H}_2$)

[Compound IId-5] $^1$H NMR (D$_2$O): 0.88 (t, 3H, C(O)CH$_2$(CH$_2$)$_{13}$C$\underline{H}_3$), 0.91 (m, peptide-H), 1.28 (m, 26H, C(H)CH$_2$(C$\underline{H}_2$)$_{13}$CH$_3$), 1.55 (m, peptide-H), 2.13 (m, peptide-H), 2.42 (m, peptide-H), 2.52 (m, 4H, C$\underline{H}_2$C$\underline{H}_2$CONH), 2.53 (t, 2H, C(O)C$\underline{H}_2$(CH$_2$)$_{13}$CH$_3$), 2.61 (m, peptide-H), 3.33 (tt, 2H, C-6-$\underline{H}_2$), 4.53 (m, peptide-H), 4.98 (s, 1H, C-5-$\underline{H}$), 5.43 (t, H, C-4-$\underline{H}_2$)

Experimental Example 1

Collagen Biosynthesis

The active ingredient substance of the present invention was added to human skin fibroblasts to test the capability of promoting collagen synthesis at the cell level.

Biosynthesis of collagen was determined by the ELISA assay method. The active ingredient substance was not added to the control group. The relative capability of promoting collagen synthesis was calculated, with that of the control group being 100%. Details are as follows.

3000 human neonatal dermal fibroblasts (Cambrex) were grouped into a 96-well plate for cell culture and were cultured for 24 hours in an incubator using DMEM (Dulbecco's Modified Eagle Media, Gibco BRL) containing 0.1% FBS (fetal bovine serum) under the condition of 37° C. and 5% CO$_2$. Each test substance was dissolved in DMEM containing 0.1% FBS to a concentration of 10 μM. After treating 200 μL of the solution, the cells were cultured for 72 hours. The supernatant was treated to a 96-well plate in which the type 1 collagen antibody was coated. After 2 hours of reaction at room temperature, the supernatant was removed. After washing with 0.05% Tween-20 PBS (PBST), a biotin-bound secondary antibody was treated in the 96-well plate at room temperature. After 1 hour of reaction, the remaining supernatant was removed. After washing with PBST, SA-HRP (streptavidin-horseradish peroxidase, Sigma) was bound to measure the bound collagen. After treating with TMB (3,3'-5,5' tetramethylbenzidine, Sigma), reaction was performed at room temperature for 15 minutes, while blocking light. Reaction was stopped using 1 N sulfuric acid and light absorbance was measured at 450 nm.

The results are shown in FIG. 1. As seen in FIG. 1, the compound Ic-1 of the present invention showed much superior capability of promoting collagen synthesis than vitamin C (Vc), magnesium ascorbyl phosphate (MAP), succinoyl ascorbyl pentapeptide (Vc-KTTKS), and palmitoyl pentapeptide (PaI-KTTKS). Also, the compounds Ic-2, Ic-3, Ic-4, and Ic-5 of the present invention had superior capability in promoting collagen synthesis. Thus, it can be seen that the compounds Ic-1, Ic-2, Ic-3, Ic-4, and Ic-5 of the present invention have superior capability of promoting collagen synthesis, in addition to improved stability.

Experimental Example 2

Cell Toxicity

In order to prove the primary safety for use as cosmetics, cell toxicity was measured for the compounds Ic-1, Ic-2, Ic-3, Ic-4, and Ic-5 of the present invention, vitamin C (Vc), magnesium ascorbyl phosphate (MAP), succinoyl ascorbyl pentapeptide (Vc-KTTKS), and palmitoyl pentapeptide (PaI-KTTKS). 3000 human neonatal dermal fibroblasts (Cambrex) were grouped into a 96-well plate for cell culture and were cultured for 24 hours in an incubator using DMEM (Gibco BRL) at 0.1% under the condition of 37° C. and 5% CO$_2$. Cell toxicity was measured 48 hours after treating with the test substance by the MTT assay (Mossman T., 1983, *Journal of Immunological Methods* 65, 55-63).

Figure 2:
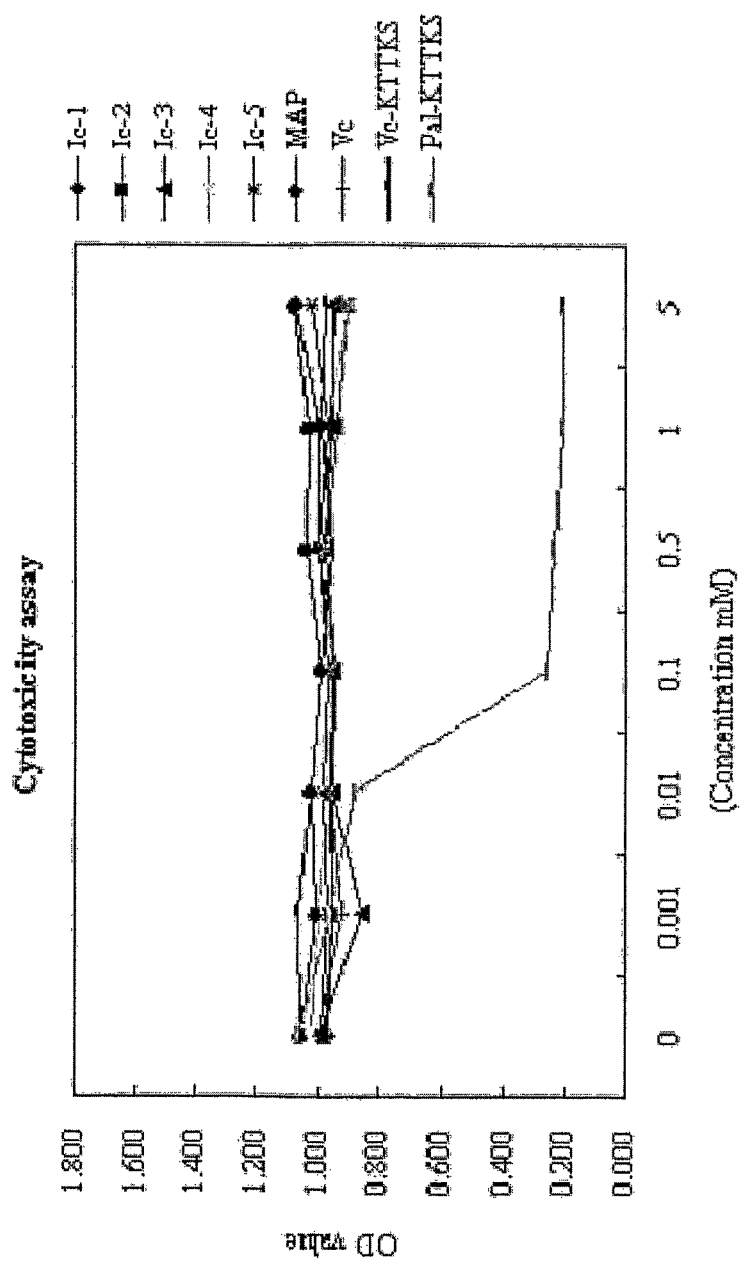
FIG. 2 shows a comparison of cell toxicity of the compound of the present invention, vitamin C, magnesium ascorbyl phosphate, succinoyl ascorbyl pentapeptide, and palmitoyl pentapeptide.

The results are shown in FIG. 2. As seen in FIG. 2, the compound Ic-1 of the present invention did not show cell toxicity even at the concentration of 5 mM, in contrast with vitamin C (Vc), succinoyl ascorbyl pentapeptide (Vc-KTTKS), and palmitoyl pentapeptide (PaI-KTTKS). In addition, the compounds Ic-2, Ic-3, Ic-4, and Ic-5 of the present invention did not show cell toxicity at 5 mM. Thus, the compound of the present invention has superior safety.

Experimental Example 3

Stability

Each of the compounds Ia-1 and Ic-1 of the present invention, vitamin C, magnesium ascorbyl phosphate, and succinoyl ascorbyl pentapeptide were dissolved in third purified water to a concentration of 10 μg/mL. Stability of each substance was evaluated, while being maintained at 25° C. and 50° C. for 30 days, by observing the change of UV (254 nm) absorbance. The obtained results are shown in Table 2.

TABLE 2

| | Ia-1 | | Ic-1 | | Vitamin C | | Magnesium ascorbyl phosphate | | Succinoyl ascorbyl phosphate | |
|---|---|---|---|---|---|---|---|---|---|---|
| Days | 25° C. | 50° C. | 25° C. | 50° C. | 25° C. | 50° C. | 25° C. | 50° C. | 25° C. | 50° C. |
| 0 | 100 | 100 | 100 | 100 | 100 | 100 | 100 | 100 | 100 | 100 |
| 1 | 100 | 100 | 100 | 100 | 1 | 0 | 100 | 100 | 60 | 50 |
| 2 | 100 | 98 | 100 | 100 | 0 | 0 | 100 | 100 | 20 | 10 |
| 3 | 100 | 97 | 100 | 100 | 0 | 0 | 100 | 100 | 10 | 0 |
| 5 | 100 | 95 | 100 | 99 | 0 | 0 | 100 | 99 | 0 | 0 |
| 10 | 99 | 90 | 100 | 99 | 0 | 0 | 100 | 99 | 0 | 0 |
| 20 | 98 | 85 | 100 | 98 | 0 | 0 | 100 | 98 | 0 | 0 |
| 30 | 97 | 80 | 100 | 98 | 0 | 0 | 100 | 98 | 0 | 0 |

Remaining test substance (%)

As seen in Table 2, the compounds of the present invention had stability superior to that of vitamin C and succinoyl ascorbyl pentapeptide. Further, they showed comparable or better stability when compared with magnesium ascorbyl phosphate, which is the most stable vitamin C derivative known thus far. In addition, the compounds of the present invention showed superior capability of collagen biosynthesis.

As can be seen from the results of Test Examples 1 to 3, the vitamin C derivative compound of the present invention shows comparable or better stability, when compared with magnesium ascorbyl phosphate, which is the most stable vitamin C derivative known thus far, and has low cell toxicity and superior capability of collagen biosynthesis. Thus, it can be used to improve skin conditions.

As is apparent from the above description, the stabilized vitamin C derivative with a collagen-producing peptide in accordance with present invention has improved stability, safety, skin permeability, etc., without toxicity such as skin irritation. With superior capability of skin improvement and prevention of aggravation of skin conditions, it can be utilized in such industrial fields as skin application medicines, cosmetics, etc.

The invention claimed is:

1. A vitamin C derivative represented by the following Chemical Formula 1, or a pharmaceutically acceptable salt thereof:

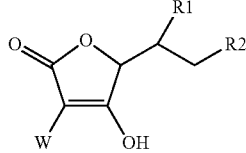

(Chemical Formula 1)

wherein
R1 and R2 are —OH or

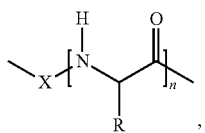

and are different from each other;

X is —OC(O)(CH$_2$)$_m$C(O)—;

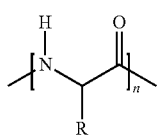

is a peptide molecule wherein identical or different amino acid residues are linked through amide bonds, and the amino acid residues are selected from the group consisting of glycine, lysine, histidine, serine, proline, hydroxyproline, threonine, glutamic acid, methionine, glutamine, and arginine;

R is a side chain of the amino acid;

n is an integer of 3 to 10;

m is an integer of 2 to 5;

W is

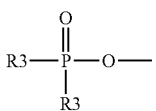

or glucose; and

R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

2. The vitamin C derivative or a pharmaceutically acceptable salt thereof according to claim 1, wherein R1 is

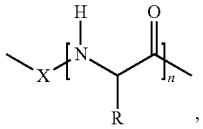

and R2 is —OH.

3. The vitamin C derivative or a pharmaceutically acceptable salt thereof according to claim 1, wherein n is an integer of 3 to 6, and m is 2.

4. The vitamin C derivative or a pharmaceutically acceptable salt thereof according to claim 3, wherein

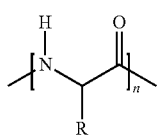

is a peptide molecule selected from glycine-histidine-lysine (SEQ ID NO: 1), glycine-lysine-histidine(SEQ ID NO: 2), glycine-proline-hydroxyproline(SEQ ID NO: 3), lysine-threonine-threonine-lysine-serine(SEQ ID NO: 4), and glutamic acid-glutamic acid-methionine-glutamine-arginine-arginine(SEQ ID NO: 5).

5. The vitamin C derivative or a pharmaceutically acceptable salt thereof according to claim 1, wherein R3 is a dimethylamine or hydroxyl group.

6. The vitamin C derivative or a pharmaceutically acceptable salt thereof according to claim 1, wherein the vitamin C derivative is selected from the group consisting of 2-tetramethylphosphorodiamidic-5-(succinyl-lysine-threonine-threonine-lysine-serine) ascorbic acid, 2-phospho-5-(succinyl-lysine-threonine-threonine-lysine-serine) ascorbic acid, 2-tetramethylphosphorodiamidic-5-(succinyl-glycine-lysine-histidine) ascorbic acid, 2-phospho-5-(succinyl-glycine-lysine-histidine) ascorbic acid, 2-tetramethylphosphorodiamidic-5-(succinyl-glycine-histidine-lysine) ascorbic acid, 2-phospho-5-(succinyl-glycine-histidine-lysine) ascorbic acid, 2-tetramethylphosphorodiamidic-5-(succinyl-glycine-proline-hydroxyproline) ascorbic acid, 2-phospho-5-(succinyl-glycine-proline-hydroxyproline) ascorbic acid 2-tetramethylphosphorodiamidic-5-(succinyl-glutamic acid-glutamic acid-methionine-glutamine-arginine-arginine) ascorbic acid, and 2-phospho-5-(succinyl-glutamic acid-glutamic acid-methionine-glutamine-arginine-arginine) ascorbic acid.

7. A vitamin C derivative represented by the following Chemical Formula 2, or a pharmaceutically acceptable salt thereof:

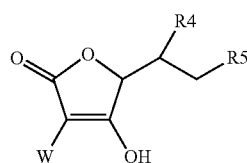

(Chemical Formula 2)

wherein
R4 and R5 are —OC(O)(CH$_2$)$_p$CH$_3$, or

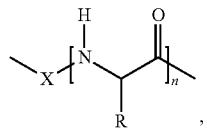

and are different from each other with the proviso that R4 and R5 are not —OC(O)(CH$_2$)$_p$CH$_3$ at the same time;
X is —OC(O)(CH$_2$)$_m$C(O)—;

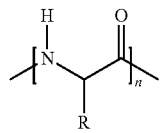

is a peptide molecule wherein identical or different amino acid residues are linked through amide bonds, and the amino acid residues are selected from the group consisting of glycine, lysine, histidine, serine, proline, hydroxyproline, threonine, glutamic acid, methionine, glutamine, and arginine;
R is a side chain of the amino acid;
n is an integer of 3 to 10;
m is an integer of 2 to 5;
p is an integer of 10 to 20;
W is

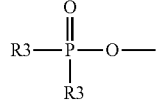

or glucose; and
R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

8. The vitamin C derivative or a pharmaceutically acceptable salt thereof according to claim 7, wherein R4 is —OC(O)(CH$_2$)$_p$CH$_3$, and R5 is

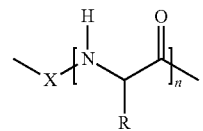

9. The vitamin C derivative or a pharmaceutically acceptable salt thereof according to claim 7, wherein n is an integer of 3 to 6, and p is 14.

10. The vitamin C derivative or a pharmaceutically acceptable salt thereof according to claim 7, wherein

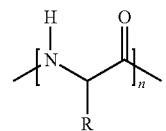

is a peptide molecule selected from the group consisting of glycine-histidine-lysine(SEQ ID NO: 1), glycine-lysine-histidine(SEQ ID NO: 2), glycine-proline-hydroxyproline(SEQ ID NO: 3), lysine-threonine-threonine-lysine-serine(SEQ ID NO: 4), and glutamic acid-glutamic acid-methionine-glutamine-arginine-arginine(SEQ ID NO: 5).

11. The vitamin C derivative or a pharmaceutically acceptable salt thereof according to claim 7, wherein R3 is dimethylamine or a hydroxyl group.

12. The vitamin C derivative or a pharmaceutically acceptable salt thereof according to claim 7, wherein the vitamin C derivative is selected from the group consisting of 2-tetramethylphosphorodiamidic-5-palmithyl-6-(succinyl-lysine-threonine-threonine-lysine-serine) ascorbic acid, 2-phospho-5-palmithyl-6-(succinyl-lysine-threonine-threonine-lysine-serine) ascorbic acid, 2-tetramethylphosphorodiamidic-5-palmithyl-6-(succinyl-glycine-lysine-histidine) ascorbic acid, 2-phospho-5-palmithyl-6-(succinyl-glycine-lysine-histidine) ascorbic acid, 2-tetramethylphosphorodiamidic-5-palmithyl-6-(succinyl-glycine-histidine-lysine) ascorbic acid, 2-phospho-5-palmithyl-6-(succinyl-glycine-histidine-lysine) ascorbic acid, 2-tetramethylphosphorodiamidic-5-palmithyl-6-(succinyl-glycine-proline-hydroxyproline) ascorbic acid, 2-phospho-5-palmithyl-6-(succinyl-glycine-proline-hydroxyproline) ascorbic acid2-tetramethylphosphorodiamidic-5-palmithyl-6-(succinyl-glutamic acid-glutamic acid-methionine-glutamine-arginine-arginine) ascorbic acid, and 2-phospho-5-palmithyl-6-(succinyl-glutamic acid-glutamic acid-methionine-glutamine-arginine-arginine) ascorbic acid.

13. A method of preparing a vitamin C derivative comprising the steps of:
(a) reacting a glucose, a phosphoryl group or a phosphate derivative represented by Chemical Formula 6 with the hydroxyl group at the 2' carbon position of vitamin C; wherein Chemical Formula 6 is

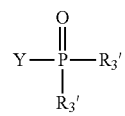

wherein R3' is selected from the group consisting of dimethylamine, diethylamine, propylamine, benzylamine; and Y is selected from the group consisting of chlorine, bromine, fluorine, and iodine;

(b) esterifying the hydroxyl group at one of the 5' or 6' carbon positions of vitamin C, with a dicarboxylic acid represented by Chemical Formula 8 to introduce the group —C(O)(CH$_2$)mCO$_2$H, wherein Chemical Formula 8 is HOOC(CH$_2$)$_m$COOH wherein m is an integer of 2 to 5; and (c) forming an amide bond by reacting —O(CO)(CH$_2$)$_m$CO$_2$H with the N-terminal amine group of a peptide molecule having 3 to 10 amino acid residues selected from the group consisting of glycine, lysine, histidine, serine, proline, hydroxyproline, threonine, glutamic acid, methionine, glutamine, and arginine, to yield:

(Chemistry Formula 1)

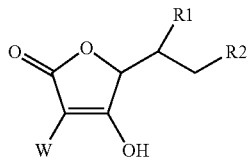

wherein R1 and R2 are —OH or

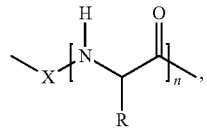

and are different from each other;
X is —OC(O)(CH$_2$)$_m$C(O)—;

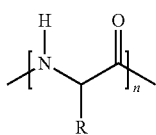

is a peptide molecule wherein identical or different amino acid residues are linked through amide bonds, and the amino acid residues are selected from the group consisting of glycine, lysine, histidine, serine, proline, hydroxyproline, threonine, glutamic acid, methionine, glutamine, and arginine;
R is a side chain of the amino acid;
n is an integer of 3 to 10;
m is an integer of 2 to 5;
W is

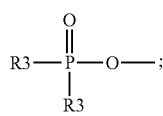

and
R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

14. The method according to claim 13, wherein the number of the amino acid residues in the peptide molecule is 3 to 6, m is 2, and Y is chlorine.

15. The method according to claim 13, wherein R3' is dimethylamine.

16. A method of preparing a vitamin C derivative comprising the steps of:
(a) reacting glucose or a phosphoryl group or a phosphate derivative represented by

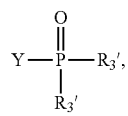

wherein R3' is selected from the group consisting of dimethylamine, diethylamine, propylamine, and benzylamine; and
Y is selected from the group consisting of chlorine, bromine, fluorine, and iodine;
with a hydroxyl group at the 2' carbon position of vitamin C;

(b) esterifying a hydroxyl group present at one of the 5' or 6' carbon positions of vitamin C, with CH$_3$(CH$_2$)$_p$COOH, wherein p is an integer of 10 to 20 and esterifying the other 5' or 6' hydroxyl group with dicarboxylic acid represented by HOOC(CH$_2$)$_m$COOH, wherein m is an integer of 2 to 5; and (c) forming an amide bond by reacting —C(O)(CH$_2$)$_m$CO$_2$H with the N-terminal amido group of a peptide molecule having 3 to 10 amino acid residues selected from the group consisting of glycine, lysine, histidine, serine, proline, hydroxyproline, threonine, glutamic acid, methionine, glutamine, and arginine, to yield

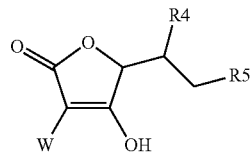

wherein R4 and R5 are —OC(O)(CH$_2$)$_p$CH$_3$, or

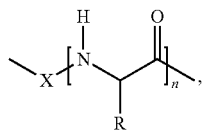

and are different from each other with the proviso that R4 and R5 are not —OC(O)(CH$_2$)$_p$CH$_3$ at the same time;
X is —OC(O)(CH$_2$)$_m$C(O)—;

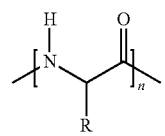

is a peptide molecule wherein identical or different amino acid residues are linked through amide bonds, and the amino acid residues are selected from the group consisting of glycine, lysine, histidine, serine, proline, hydroxyproline, threonine, glutamic acid, methionine, glutamine, and arginine;
R is a side chain of the amino acid;
n is an integer of 3 to 10;
p is an integer of 10 to 20;

W is

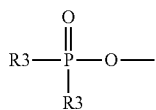

or glucose; and

R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

17. The method according to claim 16, wherein the number of the amino acid residues in the peptide molecule is 3 to 6, m is 2, and Y is chlorine.

18. The method according to claim 16, wherein R3' is dimethylamine.

19. An acylating agent of a peptide or a protein, containing a compound represented by Chemical Formula 9 or 12:

(Chemical Formula 9)

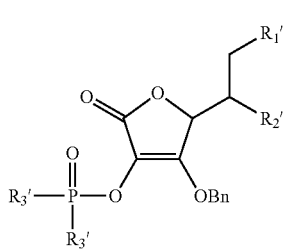

(Chemical Formula 12)

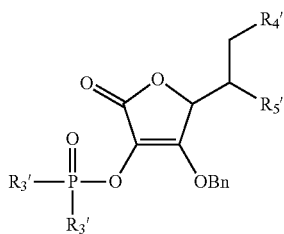

wherein
R3' is selected from the group consisting of dimethylamine, diethylamine, propylamine, and benzylamine;
R1' and R2' are —OH, or —OC(O)(CH2)mC(O)OH, and are different from each other, wherein they are not simultaneously —OH, or —OC(O)(CH2)mC(O)OH;
R4' and R5' are —OC(O)(CH$_2$)pCH$_3$ or —OC(O)(CH$_2$)mC(O)OH, and are different from each other, wherein they are not simultaneously —OC(O)(CH$_2$)pCH$_3$ or —OC(O)(CH$_2$)mC(O)OH;
m is an integer of 2 to 5; and
p is an integer of 10 to 20.

20. A method of acylating a peptide or a protein, using a compound represented by Chemical Formula 9 or 12:

(Chemical Formula 9)

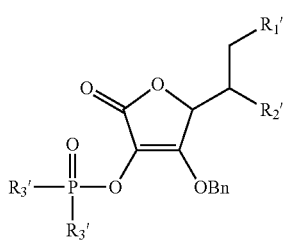

(Chemical Formula 12)

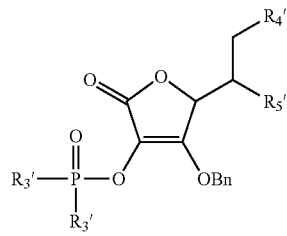

wherein
R3' is selected from the group consisting of dimethylamine, diethylamine, propylamine, and benzylamine;
R1' and R2' are —OH, or —OC(O)(CH2)mC(O)OH, and are different from each other, wherein they are not simultaneously —OH or —OC(O)(CH2)mC(O)OH;
R4' and R5' are —OC(O)(CH$_2$)pCH$_3$ or —OC(O)(CH$_2$) mC(O)OH, and are different from each other, wherein they are not simultaneously —OC(O)(CH$_2$)pCH$_3$ or —OC(O)(CH$_2$)mC(O)OH;
m is an integer of 2 to 5; and
p is an integer of 10 to 20; comprising:
(a) protecting the OH with a removable protecting group;
(b) forming an amide bond by reacting —OC(O)(CH$_2$)$_m$C(O)OH with the terminal NH$_2$ group of the peptide or protein bound to a resin at its CO$_2$H terminus;
(c) removing the protecting group on R'$_1$ or R'$_2$ and cleaving the protein or peptide from the resin to yield a compound represented by Chemical Formula 9 or 12;
wherein R1' or R2' are OH or

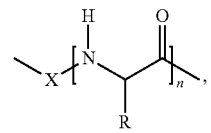

and are different from each other;
X is —OC(O)(CH$_2$)$_m$C(O)—;
R4' and R5' are —OC(O)(CH$_2$)$_p$CH$_3$ or

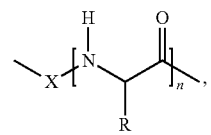

and are different from each other;
wherein

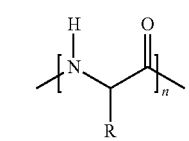

is a peptide molecule wherein identical or different amino acid residues are linked through amide bonds, and the amino acid residues are selected from the group consisting of glycine, lysine, histidine, serine, proline, hydroxyproline, threonine, glutamic acid, methionine, glutamine, and arginine;
R is a side chain of the amino acid;
n is an integer of 3 to 10; and
m is an integer of 2 to 5.

21. A composition for treating skin wrinkles comprising the vitamin C derivative of claim 1 or a pharmaceutically acceptable salt thereof as the active ingredient.

22. A composition for skin whitening comprising the vitamin C derivative of claim 1 or a pharmaceutically acceptable salt thereof as the active ingredient.

23. A method of stabilizing vitamin C, comprising the steps of:
   (a) reacting glucose, a phosphoryl group or a phosphate derivative represented by

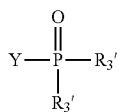

wherein R3' is selected from the group consisting of dimethylamine, diethylamine, propylamine, and benzylamine;
   Y is chlorine, bromine, fluorine, or iodine, with a hydroxyl group at the 2' carbon position of vitamin C;
   (b) reacting the dicarboxylic acid HOOC(CH3)mCOOH wherein m is an integer between 2 and 5 with the 5' or 6' hydroxyl group of vitamin C to introduce the group —OC(O)(CH$_2$)$_m$CO$_2$H at the 5' or 6' carbon position of vitamin C; and
   (c) forming an amide between the terminal amine of a peptide molecule and the —OC(O)(CH$_2$)$_m$CO$_2$H group to yield stabilized vitamin C; wherein the 5' and 6' positions of vitamin C are substituted with —OH or

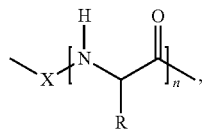

and are different from each other;

wherein X is —OC(O)(CH$_2$)$_m$C(O)—; and

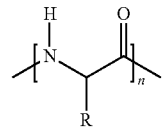

is the peptide molecule wherein identical or different amino acid residues are linked through amide bonds, and the amino acid residues are selected from the group consisting of glycine, lysine, histidine, serine, proline, hydroxyproline, threonine, glutamic acid, methionine, glutamine, and arginine;
R is a side chain of the amino acid;
n is an integer of 3 to 10;
m is an integer of 2 to 5;
W is

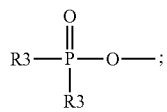

and
R3 is selected from the group consisting of —N(CH$_3$)$_2$, —N(CH$_2$CH$_3$)$_2$, —NHCH$_2$CH$_2$CH$_3$, —NHCH$_2$C$_6$H$_5$, and —OH.

24. The method according to claim 23, wherein the peptide molecule is selected from glycine-histidine-lysine (SEQ ID NO: 1), glycine-lysine-histidine (SEQ ID NO: 2), glycine-proline-hydroxyproline (SEQ ID NO: 3), lysine-threonine-threonine-lysine-serine (SEQ ID NO: 4), and glutamic acid-glutamic acid-methionine-glutamine-arginine-arginine (SEQ ID NO: 5).

* * * * *

UNITED STATES PATENT AND TRADEMARK OFFICE
CERTIFICATE OF CORRECTION

PATENT NO. : 8,829,044 B2  
APPLICATION NO. : 12/308604  
DATED : September 9, 2014  
INVENTOR(S) : Park et al.

Page 1 of 2

It is certified that error appears in the above-identified patent and that said Letters Patent is hereby corrected as shown below:

On the Title page, in item (73), in "Assignee", in column 1, line 1, delete "Peotron" and insert --Peptron--, therefor In the Claims:

In column 48, line 65, in Claim 13, delete "R3'" and insert --$R_3'$--, therefor In column 50, line 4, in Claim 15, delete "R3'" and insert --$R_3'$--, therefor In column 50, line 16, in Claim 16, delete "R3'" and insert --$R_3'$--, therefor In column 51, line 16, in Claim 18, delete "R3'" and insert --$R_3'$--, therefor In column 51, line 43, in Claim 19, delete "R3'" and insert --$R_3'$--, therefor In column 51, line 45, in Claim 19, delete "R1' and R2'" and insert --$R_1'$ and $R_2'$--, therefor In column 51, line 45, in Claim 19, delete "-OC(O)(CH2)mC(O)OH" and insert -- -OC(O)(CH$_2$)$_m$C(O)OH--, therefor In column 51, line 47, in Claim 19, delete "-OC(O)(CH2)mC(O)OH" and insert -- -OC(O)(CH$_2$)$_m$C(O)OH--, therefor In column 51, line 48, in Claim 19, delete "R4' and R5'" and insert --$R_4'$ and $R_5'$--, therefor In column 51, line 48, in Claim 19, delete "-OC(O)(CH$_2$)pCH$_3$" and insert -- -OC(O)(CH$_2$)$_p$CH$_3$--, therefor Signed and Sealed this  
Twenty-fourth Day of March, 2015

Michelle K. Lee  
*Director of the United States Patent and Trademark Office*

CERTIFICATE OF CORRECTION (continued)
U.S. Pat. No. 8,829,044 B2

In column 51, line 48-49, in Claim 19, delete "-OC(O)(CH2) mC(O)OH" and insert -- -OC(O)(CH$_2$)$_m$C(O)OH--, therefor In column 51, line 50, in Claim 19, delete "-OC(O)(CH$_2$)pCH$_3$" and insert -- -OC(O)(CH$_2$)$_p$CH$_3$--, therefor In column 51, line 51, in Claim 19, delete "-OC(O)(CH$_2$)mC(O)OH" and insert -- -OC(O)(CH$_2$)$_m$C(O)OH--, therefor In column 52, line 13, in Claim 20, delete "R3'" and insert --R$_3$'--, therefor In column 52, line 15, in Claim 20, delete "R1' and R2'" and insert --R$_1$' and R$_2$'--, therefor In column 52, line 15, in Claim 20, delete "-OC(O)(CH2)mC(O)OH" and insert -- -OC(O)(CH$_2$)$_m$C(O)OH--, therefor In column 52, line 17, in Claim 20, delete "-OC(O)(CH2)mC(O)OH" and insert -- -OC(O)(CH$_2$)$_m$C(O)OH--, therefor In column 52, line 18, in Claim 20, delete "R4' and R5'" and insert --R$_4$' and R$_5$'--, therefor In column 52, line 18, in Claim 20, delete "-OC(O)(CH$_2$)pCH$_3$" and insert -- -OC(O)(CH$_2$)$_p$CH$_3$--, therefor In column 52, line 18-19, in Claim 20, delete "-OC(O)(CH2) mC(O)OH" and insert -- -OC(O)(CH$_2$)$_m$C(O)OH--, therefor In column 52, line 20, in Claim 20, delete "-OC(O)(CH$_2$)pCH$_3$" and insert -- -OC(O)(CH$_2$)$_p$CH$_3$--, therefor In column 52, line 21, in Claim 20, delete "-OC(O)(CH$_2$)mC(O)OH" and insert -- -OC(O)(CH$_2$)$_m$C(O)OH--, therefor In column 52, line 31, in Claim 20, delete "R1' and R2'" and insert --R$_1$' and R$_2$'--, therefor In column 52, line 42, in Claim 20, delete "R4' and R5'" and insert --R$_4$' and R$_5$'--, therefor In column 53, line 18, in Claim 23, delete "R3'" and insert --R$_3$'--, therefor In column 53, line 22, in Claim 23, delete "HOOC(CH3)mCOOH" and insert --HOOC(CH$_3$)$_m$COOH--, therefor

SEQUENCE LISTING

```
<160> NUMBER OF SEQ ID NOS: 5

<210> SEQ ID NO 1
<211> LENGTH: 3
<212> TYPE: PRT
<213> ORGANISM: Artificial Sequence
<220> FEATURE:
<223> OTHER INFORMATION: Synthetic peptide molecule of glycine-
      histidine-lysine

<400> SEQUENCE: 1

Gly His Lys
 1

<210> SEQ ID NO 2
<211> LENGTH: 3
<212> TYPE: PRT
<213> ORGANISM: Artificial Sequence
<220> FEATURE:
<223> OTHER INFORMATION: Synthetic peptide molecule of glycine-lysine-
      histidine

<400> SEQUENCE: 2

Gly Lys His
 1

<210> SEQ ID NO 3
<211> LENGTH: 3
<212> TYPE: PRT
<213> ORGANISM: Artificial Sequence
<220> FEATURE:
<223> OTHER INFORMATION: Synthetic peptide molecule of glycine-proline-
      hydroxyproline
<220> FEATURE:
<221> NAME/KEY: MOD_RES
<222> LOCATION: (3)
<223> OTHER INFORMATION: hydroxyproline
```

```
<400> SEQUENCE: 3

Gly Pro Pro
 1

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide molecule of lysine-threonine-
      threonine-lysine-serine

<400> SEQUENCE: 4

Lys Thr Thr Lys Ser
 1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide molecule of glutamic acid-
      glutamic acid-methionine-glutamine-arginine-arginine

<400> SEQUENCE: 5

Glu Glu Met Gln Arg Arg
 1               5
```